(12) United States Patent
Uwai et al.

(10) Patent No.: US 7,019,157 B2
(45) Date of Patent: *Mar. 28, 2006

(54) METALLOCENE COMPOUNDS, PRODUCTION PROCESS FOR OLEFIN POLYMERS USING CATALYSTS CONTAINING THEM AND OLEFIN POLYMERS PRODUCED BY THE PRODUCTION PROCESS

(75) Inventors: Toshihiro Uwai, Ichihara (JP); Masato Nakano, Ichihara (JP); Tsutomu Ushioda, Ichihara (JP); Masami Kimura, Ichihara (JP); Tsuyoshi Yahata, Ichihara (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 238 days.

This patent is subject to a terminal disclaimer.

(21) Appl. No.: 10/210,394

(22) Filed: Aug. 2, 2002

(65) Prior Publication Data

US 2003/0149200 A1   Aug. 7, 2003

(30) Foreign Application Priority Data

| Aug. 6, 2001 | (JP) | ............................ 2001-237298 |
| Sep. 27, 2001 | (JP) | ............................ 2001-296751 |
| Nov. 22, 2001 | (JP) | ............................ 2001-357798 |
| Mar. 22, 2002 | (JP) | ............................ 2002-081232 |

(51) Int. Cl.
*C07F 17/00* (2006.01)
*C08F 4/76* (2006.01)
*C08F 4/52* (2006.01)

(52) U.S. Cl. ............................ 556/53; 556/52; 556/51; 556/11; 526/161; 526/172; 526/943

(58) Field of Classification Search ................ 526/126, 526/160, 170, 943; 556/53, 52, 161, 172
See application file for complete search history.

(56) References Cited

U.S. PATENT DOCUMENTS

| 5,064,802 | A | | 11/1991 | Stevens et al. ............. 502/155 |
| 5,278,264 | A | | 1/1994 | Spaleck et al. ............. 526/127 |
| 5,840,947 | A | * | 11/1998 | Kuber et al. .................... 556/8 |
| 6,169,051 | B1 | * | 1/2001 | Mitani et al. ................ 502/103 |
| 6,252,097 | B1 | | 6/2001 | Sugano et al. ................ 556/11 |
| 6,326,493 | B1 | * | 12/2001 | Mitani et al. ................... 546/4 |
| 6,458,982 | B1 | * | 10/2002 | Schottek et al. ............. 556/53 |
| 6,479,646 | B1 | * | 11/2002 | Nakano et al. ............... 534/10 |
| 6,492,539 | B1 | * | 12/2002 | Bingel et al. ................. 556/11 |
| 2001/0053833 | A1 | * | 12/2001 | Nakano et al. ............. 526/127 |
| 2004/0127731 | A1 | * | 7/2004 | Ushioda et al ............... 556/53 |

FOREIGN PATENT DOCUMENTS

| CA | 2084017 | 11/1992 |
| CA | 2099214 | 6/1993 |
| EP | 0 426 638 A2 | 5/1991 |
| EP | 0 427 696 A2 | 5/1991 |
| EP | 0 427 697 A2 | 5/1991 |
| EP | 0 572 003 A2 | 12/1993 |
| JP | 1-502036 | 7/1989 |
| JP | 3-179005 | 8/1991 |
| JP | 3-179006 | 8/1991 |
| JP | 3-207704 | 9/1991 |
| JP | 4-309508 | 11/1992 |
| JP | 4-353502 | 12/1992 |
| JP | 5-331232 | 12/1993 |
| JP | 6-100579 | 4/1994 |
| JP | 6-184179 | 7/1994 |
| JP | 7-149833 | 6/1995 |
| JP | 7-188318 | 7/1995 |
| JP | 8-283343 | 10/1996 |
| WO | 88/05792 | 8/1988 |
| WO | 88/05793 | 8/1988 |
| WO | 92/00333 | 1/1992 |
| WO | 93/03067 | 2/1993 |
| WO | 00/20426 | 4/2000 |
| WO | 00/43406 | 7/2000 |
| WO | WO 00/43406 A1 * | 7/2000 |

OTHER PUBLICATIONS

DE 102 35 883 (abstract only).*
"Novel Metallocene Catalyst for Propylene Polymerization," Toshihiko Sugano, SPO '99, Japanese Polychem Corporation, 1999, pp. 33-53.

(Continued)

*Primary Examiner*—David W. Wu
*Assistant Examiner*—Rip A Lee
(74) *Attorney, Agent, or Firm*—McDermott Will & Emery LLP

(57) ABSTRACT

The present invention provides metallocene compounds which exhibit high polymerization activity for production of highly stereoregular polymers, as well as a production process for olefin polymers which employs olefin polymerization catalysts containing the compounds, and olefin polymers obtained by the production process. A metallocene compound of the present invention is represented by the following general formula (1):

$$YKLMX_2 \qquad (1)$$

wherein M represents a titanium atom, zirconium atom or hafnium atom; K and L are fused rings coordinated to M and each independently represents a fused ring of a cyclopentadienyl ring and a 5-membered ring, a fused ring of a cyclopentadienyl ring and a 6-membered ring or a fused ring of a cyclopentadienyl ring and a 7-membered ring; Y is a bridge group crosslinking K and L; and each X is bonded to M; and K and L have a 2-furyl group, substituted 2-furyl group, 2-thienyl group, substituted 2-thienyl group, 2-furfuryl group or substituted 2-furfuryl group on at least one position among each of the 2-positions, 4-positions and 5-positions.

3 Claims, No Drawings

OTHER PUBLICATIONS

"Polymerization of Ethylene and Propene using New Chiral Zirconium Derivatives. Crystal Structure of [ZrL$^1$Cl$_2$]—[H$_2$L$^1$=(4S,5S)—trans- 4,5-bis(1H-inden-1-ylmethyl)-2,2,-dimethyl-1,3-dioxolane]," J. Bandy, M. Green, I. Gardiner, and K. Prout, J. Chemical Society dalton Trans. 1991, pp. 2207-2216.

"Zirconocenophane Dichlorides with Di- and Trisiloxane-Bridged Ring Ligands: Crystal Structure of rac-[1,1,3,3-tetramethyldisiloxane-diyl-bis( 3-tert-butyl-$\eta^5$cyclopentadienyl) zirconium(IV) dichloride]," J. Gräper, G. Paolucci, and R. D. Fischer, Journal of Organometallic Chemistry, 501, 1995, pp. 211-218.

"Aminozirconocenes: A New Class of Zirconocenes with a Nitrogen Atom Directly Bonded to an $\eta^5$cyclopentadienyl (indenyl) ligand," H. Plenio and D. Burth, Journal of Organometallic Chemistry, 519, 1996, pp. 269-272.

"Synthesis, Characterization and Polymerization Potential of ansa-metallocene Dichloride Complexes of Titanium, Zirconium and Hafnium Containing a Si-N-Si Bridging Unit," H. Alt, K. Föttinger, and W. Milius, Journal of Organometallic Chemistry, 564, 1998, pp. 109-114.

"Phosphorus-Bridged Metallocenes: New Homogenous Catalysts for the Polymerization of Propene," C. Schaverien, R. Ernst, W. Terlouw, P. Schut, O. Sudmeijer, and P. Budzelaar, Journal of Molecular Catalysts, 128, 1998, pp. 245-256.

"Hetero-ansa-metallocenes: I. Synthesis of the Novel [1]-borylidene-Bridged ansa-zirconocene Dichloride," K. Rufanov, V. Kotov, N. Kazennova, D. Lemenovskii, E. Avtomonov, and J. Lorberth, Journal of Organometallic Chemistry, 525, 1996, pp. 287-289.

"Propylene Homo- and Copolymerization with Ethylene Using an Ethylenebis (1-indenyl) Zirconium Dichloride and Methylaluminoxane Catalyst System," T. Tsutsui, N. Ishimaru, A. Mizuno, A. Toyota, and N. Kashiwa, Polymer, vol. 30, Jul. 1989, 1350-1356.

"Aminoborandediyl-Bridged Zirconocenes: Highly Active Olefin Polymerization Catalysts," A. Ashe, III, X. Fang, and J. Kampf, Organometallics, 18, 1999, pp. 2288-2290.

"Polyelement Subsituted Cyclopentadienes and Indenes—Novel Ligand Precursors for Organotransition Metal Chemistry," K. Rufanov, E. Avtomonov, N. Kazennova, V. Kotov, A. Khvorost, D. Lemenovskii, and J. Lorberth, Journal of Organometallic Chemistry, 1997, pp. 361-373.

"Donor Complexes of bis(1-indenyl)phenylborane Dichlorozirconium as Isospecific Catalysts in Propene Polymerization," M. Reetz, M. Willuhn, C. Psiorz, and R. Goddard, Chemical Communication, 1999, pp. 1105-1106.

"Donor/Acceptor Metallocenes: A New Structure Principle in Catalyst Design," K. Starzewski, W. M. Kelly, A. Stumpf, and D. Freitag, Agnew Chemical Int. Ed., vol. 38, No. 6, 1999, pp. 2439-2443.

"Chemistry of Hetero aromatic Compound," II, 1998, pp. 108-109.

"Characterization of Impact-Resistant Poly(Propylene-Ethylene) Copolymers by $^{13}$C Nuclear Magnetic Resonance Spectroscopy Temperature-Rising Elution Fractionation-Size Exclusion Chromotography, and Transmission Electron Microscopy," T. Usami, Y. Gotoh, H. Umemoto, and S. Takayama, Journal of Applied Polymer Science: Applied Polymer Symposium, 52, 1993, pp. 145-158.

"Carbon-13 Observations of the Stereochemical Configuration of Polyproplene," A. Zambelli, D. Dorman, A. Brewster, and F. Bovey, Macromolecules, vol. 6, No. 6, Nov.-Dec. 1973, pp. 925-926.

"Model Compounds and $^{13}$C NMR Observation of Stereosequences of Polypropylene," A. Zambelli, P. Locatelli, G. Bajo, and F. Bovey, Macromolecules, vol. 8, No. 5, Sep.-Oct. 1975, 687-689.

"Chiral Ansa Metallocenes with Cp Ring-Fused to Thiophenes and Pyrroles: Syntheses, Crystal Structures, and Isotactic Polypropylene Catalysts," J. Ewen, M. Elder, R. Jones, A. Rheingold, L. Liable-Sands, and R. Sommer, Journal of the American Chemical Society, vol. 123, 2001, pp. 4763-4773.

"Synthesis of Biological Markers in Fossil Fuels. 2. Synthesis and $^{13}$C NMR Studies of Substituted Indans and Tetralins," M. Adamczyk, D. Watt, and D. Netzel, Journal of Organic Chemistry, 49, 1984, pp. 4226-4237.

"Testing Method for Melt Flow Rate of Thermoplastics," Japanese Industrial Standard, K 7210-1976, pp. 1-16.

"Cocatalysts for Metal-Catalyzed Olefin Polymerization: Activators, Activation Processes, and Structure—Activity Relationships," E. Chen and T. Marks, Chemical Review, 100, 2001, pp. 1391-1434.

* cited by examiner

METALLOCENE COMPOUNDS, PRODUCTION PROCESS FOR OLEFIN POLYMERS USING CATALYSTS CONTAINING THEM AND OLEFIN POLYMERS PRODUCED BY THE PRODUCTION PROCESS

FIELD OF THE INVENTION

The present invention relates to metallocene compounds, to a production process for olefin polymers using olefin polymerization catalysts containing the metallocene compounds, and to olefin polymers produced by the production process.

BACKGROUND OF THE INVENTION

Propylene polymer production processes employing catalysts comprising metallocene compounds with substituted indenyl ligands are described in Japanese Patent Kokai H6-184179, Japanese Patent Kokai H6-100579 and Japanese Patent Kokai H7-188318.

These metallocene compound-containing catalysts, however, are generally costly. It has been a desired goal to further improve the polymerization activity of such catalysts in order to reduce the production cost for propylene polymers obtained using them.

Metallocene compounds of this type have been developed mainly with the aim of allowing production of high molecular weight propylene polymers and permitting a high degree of control over the stereoregularity of the resulting propylene polymers, but the desired performance has not yet been achieved to a satisfactory extent.

As has been documented by T. Sugano in SPO '99 (1999), pp.31–53, production of propylene/ethylene copolymer using a metallocene compound-containing catalyst usually results in a major decrease in molecular weight of the copolymer product as the ethylene unit content increases. A demand has existed, therefore, for development of a metallocene compound-containing catalyst which allows production of propylene/ethylene copolymer of sufficiently high molecular weight even when the ethylene unit content is high.

SUMMARY OF THE INVENTION

It is one object of the invention to provide metallocene compounds which exhibit high polymerization activity for production of highly stereoregular polymers, as well as a production process for olefin polymers which employs olefin polymerization catalysts containing the compounds, and olefin polymers obtained by the production process.

It is another object of the invention to provide metallocene compounds that allow production of high molecular weight propylene/ethylene copolymers even with a high ethylene unit content, as well as a production process for olefin polymers which employs olefin polymerization catalysts containing the compounds, and olefin polymers obtained by the production process.

It is yet another object of the invention to provide metallocene compounds that allow production of olefin polymers having few o-dichlorobenzene soluble components, so that molded articles obtained from the olefin polymers may exhibit improved tackiness and transparency, as well as a production process for olefin polymers which employs olefin polymerization catalysts containing the metallocene compounds, and olefin polymers obtained by the production process.

The present inventors have found that the aforementioned objects can be achieved by using specific metallocene compounds having specific heteroaromatic groups at specific positions, and the invention has thus been completed.

DETAILED DESCRIPTION OF THE INVENTION

The present invention provides

[1] A metallocene compound represented by the following general formula (1):

$$YKLMX_2 \quad (1)$$

wherein M represents a titanium atom, zirconium atom or hafnium atom; K and L are fused rings coordinated to M and each independently represents a fused ring of a cyclopentadienyl ring and a 5-membered ring, a fused ring of a cyclopentadienyl ring and a 6-membered ring or a fused ring of a cyclopentadienyl ring and a 7-membered ring; Y is a bridge group crosslinking K and L and represents methylene, ethylene, tetraalkylethylene with $C_1$–$C_6$ alkyl groups, dialkylmethylene with $C_1$–$C_6$ alkyl groups, or a divalent bridge group containing a silicon, germanium, oxygen, nitrogen, phosphorus or boron atom; and each X is bonded to M and represents a halogen atom, $C_1$–$C_6$ alkyl, $C_6$–$C_{16}$ aryl, alkylaryl having a $C_1$–$C_6$ alkyl group and a $C_6$–$C_{16}$ aryl group, or arylalkyl having a $C_6$–$C_{16}$ aryl group and a $C_1$–$C_6$ alkyl group. K and L each independently have on their respective 2-positions a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group;

K and L each independently also have on their respective 4-positions a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; K and L each independently also have on their respective 5-positions hydrogen, a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; with the proviso that a 2-furyl group, substituted 2-furyl group, 2-thienyl group, substituted 2-thienyl group, 2-furfuryl group or substituted 2-furfuryl group is present on at least one position among each of the 2-positions, 4-positions and 5-positions.

[2] A metallocene compound according to [1] above, represented by the following general formula (2) wherein K and L are both fused rings of a cyclopentadienyl ring and a 6-membered ring, having $R_1$ at the 2-position, $R_2$ at the 4-position and a hydrogen atom at the 5-position of each fused ring.

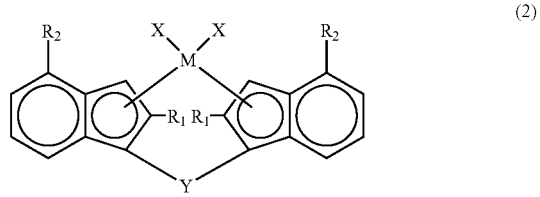

wherein each $R_1$ independently represents a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; and each $R_2$ independently represents a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; with the proviso that at least one substituent among each $R_1$ and each $R_2$ is a 2-furyl group, substituted 2-furyl group, 2-thienyl group, substituted 2-thienyl group, 2-furfuryl group or substituted 2-furfuryl group.

[3] A metallocene compound according to [2] above, wherein in general formula (2), Y is methylene, ethylene or dialkylsilylene with $C_1$–$C_6$ alkyl groups; each $R_1$ is independently a 2-furyl group, substituted 2-furyl group, 2-thienyl group, substituted 2-thienyl group, 2-furfuryl group or substituted 2-furfuryl group; and each $R_2$ is independently a $C_1$–$C_6$ alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group.

[4] A metallocene compound according to [2] above, wherein in general formula (2), each $R_1$ is independently a $C_2$–$C_6$ alkyl group, $C_1$–$C_6$ halogen-containing alkyl group, $C_1$–$C_6$ silicon-containing alkyl group, $C_6$–$C_{16}$ aryl group or $C_6$–$C_{16}$ halogen-containing aryl group; and each $R_2$ is independently a 2-furyl group, substituted 2-furyl group, 2-thienyl group, substituted 2-thienyl group, 2-furfuryl group or substituted 2-furfuryl group.

[5] A metallocene compound according to [2] above, wherein in general formula (2), each $R_1$ is methyl and each $R_2$ is independently a substituted 2-furyl group, 2-thienyl group, substituted 2-thienyl group, 2-furfuryl group or substituted 2-furfuryl group.

[6] A metallocene compound according to [2] above, wherein in general formula (2), each $R_1$ and each $R_2$ is independently a 2-furyl group, substituted 2-furyl group, 2-thienyl group, substituted 2-thienyl group, 2-furfuryl group or substituted 2-furfuryl group.

[7] A metallocene compound according to [1] above, represented by the following general formula (3) wherein K and L are both fused rings of a cyclopentadienyl ring and a 7-membered ring, having $R_3$ at the 2-position, $R_4$ at the 4-position and a hydrogen atom at the 5-position of each fused ring.

group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; with the proviso that at least one substituent among each $R_3$ and each $R_4$ is a 2-furyl group, substituted 2-furyl group, 2-thienyl group, substituted 2-thienyl group, 2-furfuryl group or substituted 2-furfuryl group.

[8] A metallocene compound according to [7] above, wherein in general formula (3), each $R_3$ is independently a $C_1$–$C_6$ alkyl group, $C_1$–$C_6$ halogen-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; each $R_4$ is independently a $C_1$–$C_6$ alkyl group, $C_6$–$C_{16}$ aryl group, 2-furyl group, substituted 2-furyl group, 2-thienyl group, substituted 2-thienyl group, 2-furfuryl group or substituted 2-furfuryl group; and when one of either $R_3$ is a 2-furyl group, substituted 2-furyl group, 2-thienyl group, substituted 2-thienyl group, 2-furfuryl group or substituted 2-furfuryl group, each $R_4$ may be, in addition to the groups mentioned above, a $C_1$–$C_6$ halogen-containing alkyl group or $C_6$–$C_{16}$ halogen-containing aryl group; with the proviso that at least one substituent among each $R_3$ and each $R_4$ is a 2-furyl group, substituted 2-furyl group, 2-thienyl group, substituted 2-thienyl group, 2-furfuryl group or substituted 2-furfuryl group.

[9] A metallocene compound according to [7] above, wherein in general formula (3), each $R_3$ is independently a 2-furyl group, substituted 2-furyl group, 2-thienyl group, substituted 2-thienyl group, 2-furfuryl group or substituted 2-furfuryl group; and each $R_4$ is independently a $C_1$–$C_6$ alkyl group, $C_6$–$C_{16}$ aryl group, $C_1$–$C_6$ halogen-containing alkyl group or $C_6$–$C_{16}$ halogen-containing aryl group.

[10] A metallocene compound according to [7] above, wherein in general formula (3), each $R_3$ is independently a $C_1$–$C_6$ alkyl group, $C_1$–$C_6$ halogen-containing alkyl group, $C_6$–$C_{16}$ aryl group or $C_6$–$C_{16}$ halogen-containing aryl group; and each $R_4$ is independently a 2-furyl group, substituted 2-furyl group, 2-thienyl group, substituted 2-thienyl group, 2-furfuryl group or substituted 2-furfuryl group.

[11] A metallocene compound according to [7] above, wherein in general formula (3), each $R_3$ and each $R_4$ is independently a 2-furyl group, substituted 2-furyl group, 2-thienyl group, substituted 2-thienyl group, 2-furfuryl group or substituted 2-furfuryl group.

[12] A metallocene compound according to [1] above, represented by the following general formula (4) wherein K and L are both fused rings of a cyclopentadienyl ring and a 5-membered ring, having $R_5$ at the 2-position, $R_6$ at the 4-position and $R_7$ at the 5-position of each fused ring.

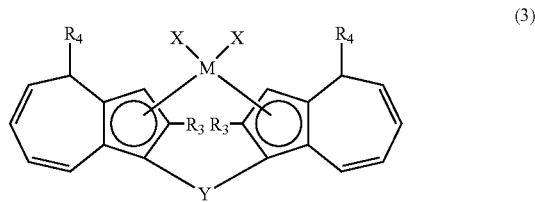

(3)

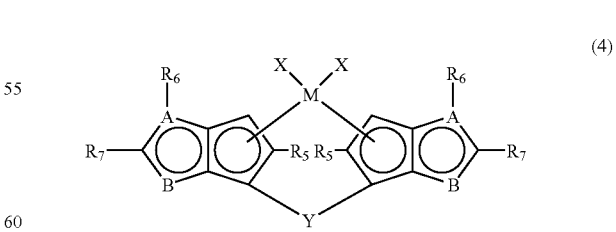

(4)

wherein each $R_3$ independently represents a $C_1$–$C_6$ alkyl group, $C_1$–$C_6$ halogen-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; and each $R_4$ independently represents a $C_1$–$C_6$ alkyl wherein each $R_5$ independently represents a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; each $R_6$ independently represents a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; and each $R_7$ independently represents hydrogen, a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; with the proviso that at least one substituent among each $R_5$, each $R_6$ and each $R_7$ is a 2-furyl group, substituted 2-furyl group, 2-thienyl group, substituted 2-thienyl group, 2-furfuryl group or substituted 2-furfuryl group. Each A independently represents a carbon atom or an atom of Group 15 of the Periodic Table and each B independently represents a carbon atom or an atom of Group 16 of the Periodic Table, with the proviso that A and B are not both carbon atoms.

[13] A metallocene compound according to [12] above, wherein in general formula (4), each $R_5$ is independently a 2-furyl group, substituted 2-furyl group, 2-thienyl group, substituted 2-thienyl group, 2-furfuryl group or substituted 2-furfuryl group, and each $R_6$ is independently a $C_1$–$C_6$ alkyl group, $C_1$–$C_6$ halogen-containing alkyl group, $C_1$–$C_6$ silicon-containing alkyl group, $C_6$–$C_{16}$ aryl group or $C_6$–$C_{16}$ halogen-containing aryl group.

[14] A metallocene compound according to [12] above, wherein in general formula (4), each $R_5$ is independently a $C_1$–$C_6$ alkyl group, $C_1$–$C_6$ halogen-containing alkyl group, $C_1$–$C_6$ silicon-containing alkyl group, $C_6$–$C_{16}$ aryl group or $C_6$–$C_{16}$ halogen-containing aryl group, and each $R_6$ is independently a 2-furyl group, substituted 2-furyl group, 2-thienyl group, substituted 2-thienyl group, 2-furfuryl group or substituted 2-furfuryl group.

[15] A metallocene compound according to [12] above, wherein in general formula (4), each $R_5$ and each $R_6$ is independently a 2-furyl group, substituted 2-furyl group, 2-thienyl group, substituted 2-thienyl group, 2-furfuryl group or substituted 2-furfuryl group.

[16] A process for production of olefin polymers, which employs an olefin polymerization catalyst comprising a metallocene compound according to any one of [1] to [15] above, an activating compound and if desired an organic aluminum compound.

[17] A process for production of olefin polymers, which employs an olefin polymerization catalyst comprising an organic aluminum compound and a supported catalyst component produced using a metallocene compound according to any one of [1] to [15] above, an activating compound, a fine particulate support and if desired an organic aluminum compound.

[18] A process for production of olefin polymers, which employs an olefin polymerization catalyst comprising an organic aluminum compound and a supported catalyst component produced using a metallocene compound according to any one of [1] to [15] above, an ion-exchangeable layer compound or inorganic silicate, and if desired an organic aluminum compound.

[19] An olefin polymer produced by a process for production of olefin polymers according to any one of [16] to [18] above.

[20] An olefin polymer according to [19] above, wherein the olefin polymer is a propylene/olefin copolymer comprising as constituent units a propylene unit and an olefin unit other than propylene, wherein the content of the olefin unit other than propylene is 0.1–80 mole percent based on the moles of the copolymer.

[21] An olefin polymer according to [20] above, wherein the olefin polymer is an olefin polymer obtained by producing in a first step a propylene homopolymer or a propylene/olefin random copolymer (I) of propylene and an olefin other than propylene, wherein the content of the olefin unit other than propylene is present at 0.1–30 mole percent based on the moles of copolymer (I), and then producing in a second step a propylene/olefin random copolymer (II) of propylene and an olefin other than propylene wherein the content of the propylene unit is 10–90 mole percent based on the moles of copolymer (II).

[22] An olefin polymer according to [21] above, wherein the melt flow rate of the propylene/olefin random copolymer (II), measured according to JIS K7210 with a load of 21.18 N and a temperature of 230° C., is no greater than 300 g/10 min.

[23] An olefin polymer according to [21] or [22] above, wherein the soluble fraction of the olefin polymer in o-dichlorobenzene at 0° C. is no greater than 30 wt % based on the weight of the polymer.

DETAILED DESCRIPTION OF THE PREFERRED EMBODIMENTS

The metallocene compounds of the invention are represented by the following general formula (1):

$$YKLMX_2 \qquad (1)$$

wherein M represents a titanium atom, zirconium atom or hafnium atom, and preferably a zirconium atom.

K and L are fused rings coordinated to M and each independently represents a fused ring of a cyclopentadienyl ring and a 5-membered ring, a fused ring of a cyclopentadienyl ring and a 6-membered ring or a fused ring of a cyclopentadienyl ring and a 7-membered ring. Preferred 5-membered rings are aromatic 5-membered rings, preferred 6-membered rings are aromatic 6-membered rings, and preferred 7-membered rings are 7-membered rings containing two double bonds in the ring structure.

Y is a bridge group crosslinking K and L and represents methylene, ethylene, tetraalkylethylene with $C_1$–$C_6$ alkyl groups, dialkylmethylene with $C_1$–$C_6$ alkyl groups, or a divalent bridge group containing a silicon, germanium, oxygen, nitrogen, phosphorus or boron atom. Alternatively, Y may be a bridge group comprised of two or more members of the foregoing in combination.

As examples of divalent bridge groups containing silicon atoms there may be mentioned dialkylsilylene groups with $C_1$–$C_6$ alkyl groups, diarylsilylene groups with $C_6$–$C_{16}$ aryl groups, dibenzylsilylene groups or alkylarylsilylene groups with $C_1$–$C_6$ alkyl groups and $C_6$–$C_{16}$ aryl groups.

As examples of divalent bridge groups containing germanium atoms there may be mentioned dialkylgermylene groups with $C_1$–$C_6$ alkyl groups, diarylgermylene groups with $C_6$–$C_{16}$ aryl groups, dibenzylgermylene groups or alkylarylgermylene groups with $C_1$–$C_6$ alkyl groups and $C_6$–$C_{16}$ aryl groups.

As examples of divalent bridge groups containing oxygen atoms there may be mentioned substituents comprising 5-membered rings with oxygen atoms in the ring structure such as described in J. Chem. Soc. Dalton Trans., 2207–2216(1991), or the groups —Si(Me)$_2$—O—Si(Me)$_2$— or —Si(Me)$_2$—O—Si(Me)$_2$—O—Si(Me)$_2$— (where "Me" is methyl) described in J. Organomet. Chem., 501, 211–218(1995).

As examples of divalent bridge groups containing nitrogen atoms there may be mentioned the group —(Me)N—(CH$_2$)$_2$—N(Me)— described in J. Organomet. Chem., 519, 269–272(1996), or the group —Si(Me)$_2$—N(C$_4$H$_9$)—Si(Me)$_2$— (where "Me" is methyl) described in J. Organomet. Chem., 564, 109–114(1998).

As examples of divalent bridge groups containing phosphorus atoms there may be mentioned the groups —P(Ph)— and —P(R)— (where "Ph" is phenyl and "R" is an alkyl group) described in J. Mol. Catal. A., 128, 245–256(1998).

Examples of divalent bridge groups containing boron atoms which may be used include the group —B(Ph)— (where "Ph" is phenyl) described in J. Organomet. Chem., 525, 287–289(1996), the groups —B(N(i-Pr)$_2$)—(where "i-Pr" is isopropyl), —B(NMe$_2$)— and —B(NMe$_2$)—B—(NMe$_2$)— described in Organometallics, 18, 2288–2290 (1999) and WO00/20426, the group —B(C(SiMe$_3$)$_3$)— (where "Me" is methyl) described in J. Organomet. Chem., 536–537, 361–373(1997), the group —B(Ph) (L)— (where "Ph" is phenyl and "L" is OEt$_2$, PME$_3$ or a 5-membered ring containing oxygen in the ring structure) described in Chem. Commun., 1105–1106(1999), or a bridge group having the following general, formula:

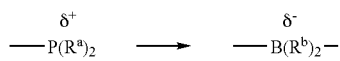

where R$_a$ is preferably C$_1$–C$_6$ alkyl and R$_b$ is preferably a halogen atom, as described in Angew. Chem. Int. Ed., 38, No.6, 2439–2443 (1999).

Preferred as the bridge group Y are methylene, ethylene, dialkylsilylene, dialkylgermylene, tetraalkylethylene or dialkylmethylene groups with C$_1$–C$_6$ alkyl groups, diarylsilylene or diarylgermylene groups with C$_6$–C$_{16}$ aryl groups, or alkylarylsilylene or alkylarylgermylene groups with C$_1$–C$_6$ alkyl groups and C$_6$–C$_{16}$ aryl groups. Dimethylsilylene or dimethylgermylene are most preferred.

Each X is independently an M-bonded halogen atom, C$_1$–C$_6$ alkyl, C$_6$–C$_{16}$ aryl, alkylaryl having a C$_1$–C$_6$ alkyl group and a C$_6$–C$_{16}$ aryl group, or arylalkyl having a C$_6$–C$_{16}$ aryl group and a C$_1$–C$_6$ alkyl group. Alternatively, as described in Example 12 in WO00/20426, two X's together may form a diene compound with such structure that the two double bonds of the diene compound are respectively coordinated to M. The diene compound preferably has a butadiene skeleton, and 1,4-diphenyl-1,3-butadiene is particularly preferred. Among the aforementioned groups, X is most preferably a chlorine atom.

K and L each independently have on their respective 2-positions a C$_1$–C$_6$ alkyl group, C$_1$–C$_6$ halogen-containing alkyl group, C$_1$–C$_6$ silicon-containing alkyl group, C$_6$–C$_{16}$ aryl group, C$_6$–C$_{16}$ halogen-containing aryl group, 2-furyl group, substituted 2-furyl group, 2-thienyl group, substituted 2-thienyl group, 2-furfuryl group or substituted 2-furfuryl group;

K and L each independently also have on their respective 4-positions a C$_1$–C$_6$ alkyl group, C$_1$–C$_6$ halogen-containing alkyl group, C$_1$–C$_6$ silicon-containing alkyl group, C$_6$–C$_{16}$ aryl group, C$_6$–C$_{16}$ halogen-containing aryl group, 2-furyl group, substituted 2-furyl group, 2-thienyl group, substituted 2-thienyl group, 2-furfuryl group or substituted 2-furfuryl group K and L each independently also have on their respective 5-positions hydrogen, a C$_1$–C$_6$ alkyl group, C$_1$–C$_6$ halogen-containing alkyl group, C$_1$–C$_6$ silicon-containing alkyl group, C$_6$–C$_{16}$ aryl group, C$_6$–C$_{16}$ halogen-containing aryl group, 2-furyl group, substituted 2-furyl group, 2-thienyl group, substituted 2-thienyl group, 2-furfuryl group or substituted 2-furfuryl group.

However, a 2-furyl group, substituted 2-furyl group, 2-thienyl group, substituted 2-thienyl group, 2-furfuryl group or substituted 2-furfuryl group must be present on at least one position among each of the 2-positions, 4-positions and 5-positions.

According to the invention, a "substituted 2-furyl group", "substituted 2-thienyl group" or "substituted 2-furfuryl group" is a group wherein a hydrogen atom bonded to a carbon forming the basic structure of a 2-furyl, 2-thienyl and 2-furfuryl group, respectively, is substituted with a substituent. Preferred as the "substituent" is a hydrocarbon, silicon-containing hydrocarbon or halogen-containing hydrocarbon group of preferably 1–20 carbons and more preferably 1–6 carbons. Additional substituents that may be used include halogen atoms, SR, SO$_2$H, SO$_2$R, COOH, COOR, NO$_2$, BR$_2$, COR, CHO, C(OH)R$_2$, CH$_2$CH$_2$OH, PO(OR)$_2$ and the like, and the synthesis method may be as described by, for example, Yamanaka, H. et al. in "Heterocyclic Compound Chemistry", 2nd Printing (1998), p.108. In the above list of substituents, R represents a hydrocarbon group of 1–20 carbons.

Preferred substituted 2-furyl groups according to the invention are, specifically, 2-(5-methyl)-furyl, 2-(5-t-butyl)-furyl, 2-(5-trimethylsilyl)-furyl, 2-(4,5-dimethyl)-furyl, 2-(5-phenyl)-furyl and 2-benzofuryl.

Preferred substituted 2-thienyl groups according to the invention are, specifically, 2-(5-methyl)-thienyl, 2-( 5-t-butyl) -thienyl, 2-(5-trimethylsilyl) -thienyl, 2-(4,5-dimethyl) -thienyl, 2-(5-phenyl)-thienyl and 2-benzothienyl.

Preferred substituted 2-furfuryl groups according to the invention are, specifically, 2-furfuryl wherein the 5-position hydrogen of the furyl group is substituted with methyl, t-butyl, trimethylsilyl or phenyl, or wherein the 4- and 5-position hydrogen is both substituted with methyl.

One of the preferred embodiment among the metallocene compounds of the invention represented by general formula (1) above are metallocene compounds represented by the following general formula (2).

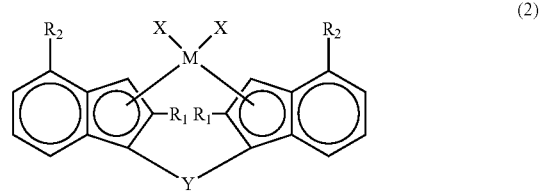

wherein each R$_1$ independently represents a C$_1$–C$_6$ alkyl group, C$_1$–C$_6$ halogen-containing alkyl group, C$_1$–C$_6$ silicon-containing alkyl group, C$_6$–C$_{16}$ aryl group, C$_6$–C$_{16}$ halogen-containing aryl group, 2-furyl group, substituted 2-furyl group, 2-thienyl group, substituted 2-thienyl group, 2-furfuryl group or substituted 2-furfuryl group. The C$_6$–C$_{16}$ aryl group may, if desired, be substituted with one or more C$_1$–C$_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

Each R$_2$ independently represents a C$_1$–C$_6$ alkyl group, C$_1$–C$_6$ halogen-containing alkyl group, C$_1$–C$_6$ silicon-containing alkyl group, C$_6$–C$_{16}$ aryl group, C$_6$–C$_{16}$ halogen-containing aryl group, 2-furyl group, substituted 2-furyl group, 2-thienyl group, substituted 2-thienyl group, 2-furfuryl group or substituted 2-furfuryl group. The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

At least one substituent among each $R_1$ and each $R_2$ is a 2-furyl group, substituted 2-furyl group, 2-thienyl group, substituted 2-thienyl group, 2-furfuryl group or substituted 2-furfuryl group.

A metallocene compound of general formula (2) may have a $C_1$–$C_6$ alkyl group, $C_1$–$C_6$ silicon-containing hydrocarbon group, $C_1$–$C_6$ halogen-containing hydrocarbon group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group at either or both of the 6- and 7-positions of the fused rings, so long as the effect of the invention is not hindered. Metallocene compounds of general formula (2) having substituents at the 7-position are particularly preferred since they allow production of very highly stereoregular olefin polymers when used as olefin polymerization catalyst components.

The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

One of the preferred embodiment among the metallocene compounds of general formula (2) are metallocene compounds wherein Y is methylene, ethylene, dialkylsilylene with $C_1$–$C_6$ alkyl groups, and preferably dimethylsilylene; each $R_1$ is independently 2-furyl, substituted 2-furyl, 2-thienyl, substituted 2-thienyl, 2-furfuryl or substituted 2-furfuryl, preferably substituted 2-furyl, and more preferably both are 2-(5-methyl)-furyl; each $R_2$ is independently $C_1$–$C_6$ alkyl, $C_6$–$C_{16}$ aryl, $C_6$–$C_{16}$ halogen-containing aryl, 2-furyl, substituted 2-furyl, 2-thienyl, substituted 2-thienyl, 2-furfuryl or substituted 2-furfuryl, preferably $C_6$–$C_{16}$ aryl or $C_6$–$C_{16}$ halogen-containing aryl, more preferably phenyl, chlorophenyl, naphthyl or phenanthryl, and most preferably both are phenyl.

These metallocene compounds may be especially preferably used as olefin polymerization catalyst components to produce high molecular weight and highly stereoregular olefin polymers, with high polymerization activity. These metallocene compounds may also be especially preferably used as olefin polymerization catalyst components for copolymerization of propylene and olefins other than propylene, with virtually no or less reduction in molecular weight of the resulting propylene/olefin copolymers even when the content of the olefin unit other than propylene is increasing, thereby allowing production of propylene/olefin copolymers of equivalent molecular weight to propylene homopolymers produced under the same conditions. Such metallocene compounds may also be especially preferably used as olefin polymerization catalyst components for copolymerization of propylene and olefins other than propylene, to produce random copolymers or random block copolymers with few soluble components in o-dichlorobenzene.

As specific compounds there may be mentioned dimethylsilylenebis(2-(2-furyl)-4-phenyl-indenyl)zirconium dichloride, dimethylsilylenebis(2-(2-(5-methyl)-furyl)-4-phenyl-indenyl)zirconium dichloride, diphenylsilylenebis(2-(2-(5-methyl)-furyl)-4-phenyl-indenyl)zirconium dichloride, dimethylgermylenebis(2-(2-(5-methyl)-furyl)-4-phenyl-indenyl)zirconium dichloride, dimethylsilylenebis(2-(2-(5-t-butyl)-furyl)-4-phenyl-indenyl)zirconium dichloride, dimethylsilylenebis(2-(2-(5-trimethylsilyl)-furyl)-4-phenyl-indenyl)zirconium dichloride, dimethylsilylenebis(2-(2-(5-phenyl)-furyl)-4-phenyl-indenyl)zirconium dichloride, dimethylsilylenebis(2-(2-(4,5-dimethyl)-furyl)-4-phenyl-indenyl)zirconium dichloride, dimethylsilylenebis(2-(2-benzofuryl)-4-phenyl-indenyl)zirconium dichloride, diphenylsilylenebis(2-(2-(5-methyl)-furyl)-4-phenyl-indenyl)zirconium dichloride, dimethylsilylenebis(2-(2-(5-methyl)-furyl)-4-methyl-indenyl)zirconium dichloride or dimethylsilylenebis(2-(2-(5-methyl)-furyl)-4-isopropyl-indenyl)zirconium dichloride, dimethylsilylenebis(2-(2-furfuryl)-4-phenyl-indenyl)zirconium dichloride, dimethylsilylenebis(2-(2-(5-methyl)-furyl)-4-(4-chlorophenyl)-indenyl)zirconium dichloride, dimethylsilylenebis(2-(2-(5-methyl)-furyl)-4-(4-fluorophenyl)-indenyl)zirconium dichloride, dimethylsilylenebis(2-(2-(5-methyl)-furyl)-4-(4-trifluoromethylphenyl)-indenyl)zirconium dichloride, dimethylsilylenebis(2-(2-(5-methyl)-furyl)-4-(4-t-butylphenyl)-indenyl)zirconium dichloride, dimethylsilylenebis(2-(2-furyl)-4-naphthyl-indenyl)zirconium dichloride, dimethylsilylenebis(2-(2-furyl)-4-phenanthryl-indenyl)zirconium dichloride, dimethylsilylenebis(2-(2-(5-methyl)-furyl)-4-naphthyl-indenyl)zirconium dichloride, dimethylsilylenebis(2-(2-(5-methyl)-furyl)-4-phenanthryl-indenyl) zirconium dichloride, dimethylsilylenebis(2-(2-(5-t-butyl)-furyl)-4-naphthyl-indenyl)zirconium dichloride and dimethylsilylenebis(2-(2-(5-t-butyl)-furyl)-4-phenanthryl-indenyl)zirconium dichloride.

Preferred among these are dimethylsilylenebis(2-(2-(5-methyl)-furyl)-4-phenyl-indenyl)zirconium dichloride, or dimethylsilylenebis(2-(2-(5-methyl)-furyl)-4-naphthyl-indenyl)zirconium dichloride. Especially preferably, dimethylsilylenebis(2-(2-(5-methyl)-furyl)-4-phenyl-indenyl)zirconium dichloride.

Another preferred embodiment among the metallocene compounds represented by general formula (2) are metallocene compounds wherein each R, is independently $C_2$–$C_6$ alkyl, $C_1$–$C_6$ halogen-containing alkyl, $C_1$–$C_6$ silicon-containing alkyl, $C_6$–$C_{16}$ aryl or $C_6$–$C_{16}$ halogen-containing aryl, preferably $C_2$–$C_6$ alkyl, more preferably ethyl, isopropyl, n-butyl or t-butyl and even more preferably both are ethyl, isopropyl or n-butyl; each $R_2$ is independently 2-furyl, substituted 2-furyl, 2-thienyl, substituted 2-thienyl, 2-furfuryl or substituted 2-furfuryl, preferably substituted 2-furyl or substituted 2-thienyl, and more preferably both are 2-(5-methyl)-furyl or 2-(5-methyl)-thienyl. These metallocene compounds may be especially preferably used as olefin polymerization catalyst components to produce high molecular weight and highly stereoregular olefin polymers, with high polymerization activity.

Specific examples of such metallocene compounds include dimethylsilylenebis(2-ethyl-4-(2-furyl)-indenyl)zirconium dichloride, dimethylsilylenebis(2-ethyl-4-(2-(5-methyl)-furyl)-indenyl)zirconium dichloride, dimethylsilylenebis(2-ethyl-4-(2-(5-t-butyl)-furyl)-indenyl)zirconium dichloride, dimethylsilylenebis(2-ethyl-4-(2-(5-trimethylsilyl)-furyl)-indenyl)zirconium dichloride, dimethylsilylenebis(2-ethyl-4-(2-benzofuryl)-indenyl)zirconium dichloride, dimethylsilylenebis(2-ethyl-4-(2-(4,5-dimethyl)-furyl)-indenyl)zirconium dichloride, dimethylsilylenebis(2-ethyl-4-(2-furfuryl)-indenyl)zirconium dichloride, dimethylsilylenebis(2-ethyl-4-(2-thienyl)-indenyl)zirconium dichloride, dimethylsilylenebis(2-ethyl-4-(2-(5-methyl)-thienyl)-indenyl)zirconium dichloride, dimethylsilylenebis(2-ethyl-4-(2-(5-t-butyl)-thienyl)-indenyl)zirconium dichloride, dimethylsilylenebis(2-ethyl-4-(2-(5-trimethylsilyl)-thienyl)-indenyl)zirconium dichloride, dimethylsilylenebis(2-ethyl-4-(2-benzothienyl)-indenyl)zirconium dichloride, dimethylsilylenebis(2-ethyl-4-(2-(4,5-dimethyl)- thienyl)-indenyl)zirconium dichloride, dimethylsilylenebis (2-(isopropyl)-4-(2-furyl)-indenyl)zirconium dichloride, dimethylsilylenebis(2-(isopropyl)-4-(2-(5-methyl)-furyl)-indenyl)zirconium dichloride, dimethylsilylenebis(2-(isopropyl)-4-(2-(5-t-butyl)-furyl)-indenyl)zirconium dichloride, dimethylsilylenebis(2-(isopropyl)-4-(2-(5-trimethylsilyl)-furyl)-indenyl)zirconium dichloride, dimethylsilylenebis(2-(isopropyl)-4-(2-benzofuryl)-indenyl)zirconium dichloride, dimethylsilylenebis(2-(isopropyl)-4-(2-(4,5-dimethyl)-furyl)-indenyl)zirconium dichloride, dimethylsilylenebis(2-(isopropyl)-4-(2-furfuryl)-indenyl)zirconium dichloride, dimethylsilylenebis(2-(n-butyl)-4-(2-(5-methyl)-furyl)-indenyl)zirconium dichloride, dimethylsilylenebis(2-(t-butyl)-4-(2-(5-methyl)-furyl)-indenyl)zirconium dichloride, dimethylgermylenebis(2-ethyl-4-(2-(5-methyl)-furyl)-indenyl)zirconium dichloride, and diphenylsilylenebis(2-ethyl-4-(2-(5-methyl)-furyl)-indenyl)zirconium dichloride.

Another preferred embodiment among the metallocene compounds represented by general formula (2) are metallocene compounds wherein $R_1$ is methyl, and $R_2$ is substituted 2-furyl, 2-thienyl, substituted 2-thienyl, 2-furfuryl or substituted 2-furfuryl, preferably substituted 2-furyl, and more preferably both are 2-(5-methyl)-furyl. These metallocene compounds may be especially preferably used as olefin polymerization catalyst components to produce high molecular weight and highly stereoregular olefin polymers, with high polymerization activity.

Specific examples of such metallocene compounds include dimethylsilylenebis(2-methyl-4-(2-(5-methyl)-furyl)-indenyl)zirconium dichloride, dimethylsilylenebis(2-methyl-4-(2-(5-t-butyl)-furyl)-indenyl)zirconium dichloride, dimethylsilylenebis(2-methyl-4-(2-(5-trimethylsilyl)-furyl)-indenyl)zirconium dichloride, dimethylsilylenebis(2-methyl- 4-(2-benzofuryl)-indenyl)zirconium dichloride, dimethylsilylenebis(2-methyl-4-(2-(4,5-dimethyl)-furyl)-indenyl)zirconium dichloride, dimethylsilylenebis(2-methyl-4-(2-furfuryl)-indenyl)zirconium dichloride, dimethylsilylenebis(2-methyl-4-(2-thienyl)-indenyl)zirconium dichloride, dimethylsilylenebis (2-methyl-4- (2- (5-methyl) -thienyl)-indenyl)zirconium dichloride, dimethylsilylenebis(2-methyl-4-(2-(5-t-butyl)-thienyl)-indenyl)zirconium dichloride, dimethylsilylenebis(2-methyl-4-(2-(5-trimethylsilyl)-thienyl)-indenyl)zirconium dichloride, dimethylsilylenebis(2-methyl-4-(2-benzothienyl)-indenyl)zirconium dichloride and dimethylsilylenebis(2-methyl-4-(2-(4,5-dimethyl)-thienyl)-indenyl)zirconium dichloride.

Another preferred embodiment among the metallocene compounds represented by general formula (2) are metallocene compounds wherein each $R_1$ and each $R_2$ is independently 2-furyl, substituted 2-furyl, 2-thienyl, substituted 2-thienyl, 2-furfuryl or substituted 2-furfuryl, more preferably both are substituted 2-furyl, and even more preferably both are 2-(5-methyl)-furyl.

These metallocene compounds may be especially preferably used as olefin polymerization catalyst components to produce high molecular weight and highly stereoregular olefin polymers, with high polymerization activity. When used as olefin polymerization catalyst components, these metallocene compounds allow production of olefin polymers having large values for both the proportion of moles of the olefin unit derived from 2,1-insertion reaction of the olefin with respect to the total moles of the olefin unit of the olefin polymer and the proportion of moles of the olefin unit derived from 1,3-insertion reaction of the olefin with respect to the total moles of the olefin unit of the olefin polymer, and in particular, they allow easy production of olefin polymers wherein the former proportion is in the range of greater than 0.5 mole percent and less than 3 mole percent while the latter proportion is in the range of greater than 0.05 mole percent and less than 3 mole percent. Molded articles obtained using olefin polymers having such properties exhibit excellent flexibility, transparency and gloss.

Specific examples of such metallocene compounds include dimethylsilylenebis(2-(2-furyl)-4-(2-furyl)-indenyl) zirconium dichloride, dimethylsilylenebis(2-(2-furyl)-4-(2-(5-methyl)-furyl)-indenyl)zirconium dichloride, dimethylsilylenebis(2-(2-furyl)-4-(2-(5-t-butyl)-furyl)-indenyl) zirconium dichloride, dimethylsilylenebis(2-(2-furyl)-4-(2-(5-trimethylsilyl)-furyl)-indenyl)zirconium dichloride, dimethylsilylenebis(2-(2-furyl)-4-(2-benzofuryl)-indenyl) zirconium dichloride, dimethylsilylenebis(2-(2-furyl)-4-(2-(4,5-dimethyl)-furyl)-indenyl)zirconium dichloride, dimethylsilylenebis(2-(2-furfuryl)-4-naphthyl-indenyl)zirconium dichloride, dimethylsilylenebis(2-(2-furfuryl)-4-(2-furfuryl)-indenyl)zirconium dichloride, dimethylsilylenebis(2-(2-furyl)-4-(2-furfuryl)-indenyl)zirconium dichloride, dimethylsilylenebis(2-(2-(5-methyl)-furyl)-4-(2-furyl)-indenyl) zirconium dichloride, dimethylsilylenebis(2-(2-(5-methyl)-furyl)-4-(2,-(5-methyl)-furyl)-indenyl)zirconium dichloride, dimethylsilylenebis(2-(2-(5-methyl)-furyl)-4-(2-(5-t-butyl)-furyl)-indenyl)zirconium dichloride, dimethylsilylenebis(2-(2-(5-methyl)-furyl)-4-(2-(5-trimethylsilyl)-furyl)-indenyl) zirconium dichloride, dimethylsilylenebis(2-(2-(5-methyl)-furyl)-4-(2-(4,5-dimethyl)-furyl)-indenyl)zirconium dichloride.

Another preferred embodiment among the metallocene compounds of the invention represented by general formula (1) are metallocene compounds represented by the following general formula (3).

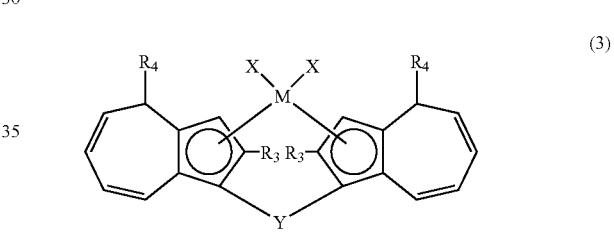

(3)

wherein each $R_3$ independently represents a $C_1$–$C_6$ alkyl group, $C_1$–$C_6$ halogen-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group. The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

Preferred as $R_3$ are $C_1$–$C_6$ alkyl, 2-furyl or substituted 2-furyl groups. More preferred are methyl, ethyl, isopropyl, n-butyl, t-butyl, 2-furyl or substituted 2-furyl. Among these, methyl and substituted 2-furyl are especially preferred.

Each $R_4$ independently represents a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group. The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

Preferred as $R_4$ are $C_1$–$C_6$ alkyl, $C_6$–$C_{16}$ aryl, 2-furyl, substituted 2-furyl, 2-thienyl or substituted 2-thienyl groups. More preferred are $C_6$–$C_{16}$ aryl, 2-furyl, substituted 2-furyl, 2-thienyl or substituted 2-thienyl groups. Still more preferred are phenyl, naphthyl, phenanthryl, 2-thienyl or substituted 2-thienyl. Most preferred are 2-thienyl and substituted 2-thienyl.

At least one substituent among each $R_3$ and each $R_4$ is a 2-furyl group, substituted 2-furyl group, 2-thienyl group, substituted 2-thienyl group, 2-furfuryl group or substituted 2-furfuryl group.

A metallocene compound of general formula (3) may have a $C_1$–$C_6$ alkyl group, $C_1$–$C_6$ silicon-containing hydrocarbon group, $C_1$–$C_6$ halogen-containing hydrocarbon group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group at any or all of the 6-, 7- and 8-positions of the fused rings, so long as the effect of the invention is not hindered. Metallocene compounds of general formula (3) having substituents at the 7-position are particularly preferred since they allow production of very highly stereoregular olefin polymers when used as olefin polymerization catalyst components.

The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

Preferred metallocene compounds of general formula (3) are metallocene compounds wherein each $R_3$ independently represents a $C_1$–$C_6$ alkyl group, $C_1$–$C_6$ halogen-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group; each $R_4$ independently represents a $C_1$–$C_6$ alkyl group, $C_6$–$C_{16}$ aryl group, 2-furyl group, substituted 2-furyl group, 2-thienyl group, substituted 2-thienyl group, 2-furfuryl group or substituted 2-furfuryl group; and when at least one of the $R_3$ is a 2-furyl group, substituted 2-furyl group, 2-thienyl group, substituted 2-thienyl group, 2-furfuryl group or substituted 2-furfuryl group, each $R_4$ may be, in addition to the groups mentioned above, a $C_1$–$C_6$ halogen-containing alkyl group or $C_6$–$C_{16}$ halogen-containing aryl group; with the proviso that at least one substituent among each $R_3$ and each $R_4$ is a 2-furyl group, substituted 2-furyl group, 2-thienyl group, substituted 2-thienyl group, 2-furfuryl group or substituted 2-furfuryl group.

These compounds may be preferably used as olefin polymerization catalyst components to produce highly stereoregular olefin polymers. These compounds may also be preferably used as olefin polymerization catalyst components to produce high molecular weight and highly stereoregular olefin polymers, with high polymerization activity. Also when catalyst systems containing such compounds are used for copolymerization of propylene and olefin other than propylene, a excellent advantage is provided in that there is virtually no or less reduction in molecular weight of the resulting propylene/olefin copolymers in spite of comprising the olefin unit other than propylene, but instead they allow production of propylene/olefin copolymers of high molecular weight comparable to propylene homopolymers produced under the same conditions.

One of the preferred embodiment among the metallocene compounds represented by general formula (3) are metallocene compounds wherein each $R_3$ is independently 2-furyl, substituted 2-furyl, 2-thienyl, substituted 2-thienyl, 2-furfuryl or substituted 2-furfuryl, preferably 2-furyl or substituted 2-furyl, and more preferably both are substituted 2-furyl and especially 2-(5-methyl)-furyl; each $R_4$ is independently $C_1$–$C_6$ alkyl, $C_6$–$C_{16}$ aryl, $C_1$–$C_6$ halogen-containing alkyl or $C_6$–$C_{16}$ halogen-containing aryl, preferably $C_6$–$C_{16}$ aryl or $C_6$–$C_{16}$ halogen-containing aryl, more preferably phenyl, chlorophenyl, naphthyl or phenanthryl, and most preferably both are phenyl. These compounds may be preferably used as olefin polymerization catalyst components to produce high molecular weight and highly stereoregular olefin polymers, with high polymerization activity. Also, when catalyst systems containing such compounds are used for copolymerization of propylene and olefin other than propylene, a excellent advantage is provided in that there is virtually no or less reduction in molecular weight of the resulting propylene/olefin copolymers in spite of comprising the olefin unit other than propylene, but instead they allow production of propylene/olefin copolymers of high molecular weight comparable to propylene homopolymers produced under the same conditions.

Specific examples of such metallocene compounds include dimethylsilylenebis(2-(2-furyl)-4-phenyl-4-hydroazulenyl)zirconium dichloride, dimethylsilylenebis(2-(2-(5-methyl)-furyl)-4-phenyl-4-hydroazulenyl)zirconium dichloride, diphenylsilylenebis(2-(2-(5-methyl)-furyl)-4-phenyl-4-hydroazulenyl)zirconium dichloride, dimethylgermylenebis(2-(2-(5-methyl)-furyl)-4-phenyl-4-hydroazulenyl)zirconium dichloride, dimethylsilylenebis(2-(2-(5-methyl)-furyl)-4-(4-chlorophenyl)-4-hydroazulenyl)zirconium dichloride, dimethylsilylenebis(2-(2-(5-methyl)-furyl)-4-(3-chlorophenyl)-4-hydroazulenyl)zirconium dichloride, dimethylsilylenebis(2-(2-(5-methyl)-furyl)-4-(4-fluorophenyl)-4-hydroazulenyl)zirconium dichloride, dimethylsilylenebis(2-(2-(5-methyl)-furyl)-4-(4-trifluoromethylphenyl)-4-hydroazulenyl)zirconium dichloride, dimethylsilylenebis(2-(2-(5-t-butyl)-furyl)-4-phenyl-4-hydroazulenyl)zirconium dichloride, dimethylsilylenebis(2-(2-(5-trimethylsilyl)-furyl)-4-phenyl-4-hydroazulenyl)zirconium dichloride, dimethylsilylenebis(2-(2-(5-phenyl)-furyl)-4-phenyl-4-hydroazulenyl)zirconium dichloride, dimethylsilylenebis(2-(2-(4,5-dimethyl)-furyl)-4-phenyl-4-hydroazulenyl)zirconium dichloride, dimethylsilylenebis(2-(2-benzofuryl)-4-phenyl-4-hydroazulenyl)zirconium dichloride, diphenylsilylenebis(2-(2-(5-methyl)-furyl)-4-phenyl-4-hydroazulenyl)zirconium dichloride, dimethylsilylenebis(2-(2-(5-methyl)-furyl)-4-methyl-4-hydroazulenyl)zirconium dichloride or dimethylsilylenebis(2-(2-(5-methyl)-furyl)-4-isopropyl-4-hydroazulenyl)zirconium dichloride, dimethylsilylenebis(2-methyl-4-(2-(5-methyl)-furyl)-indenyl)zirconium dichloride, dimethylsilylenebis(2-(2-furfuryl)-4-phenyl-4-hydroazulenyl)zirconium dichloride and dimethylsilylenebis(2-(2-(5-methyl)-furyl)-4-((3,5-ditrifluoromethyl)-phenyl)-4-hydroazulenyl)zirconium dichloride.

Preferred is dimethylsilylenebis(2-(2-(5-methyl)-furyl)-4-phenyl-4-hydroazulenyl)zirconium dichloride.

Another preferred embodiment among the metallocene compounds represented by general formula (3) are metallocene compounds wherein each $R_3$ is independently $C_1$–$C_6$ alkyl, $C_1$–$C_6$ halogen-containing alkyl, $C_6$–$C_{16}$ aryl or $C_6$–$C_{16}$ halogen-containing aryl, preferably $C_1$–$C_6$ alkyl, more preferably methyl or ethyl, and even more preferably both are methyl; each $R_4$ is independently 2-furyl, substituted 2-furyl, 2-thienyl, substituted 2-thienyl, 2-furfuryl or substituted 2-furfuryl, preferably 2-furyl, substituted 2-furyl, 2-thienyl or substituted 2-thienyl, and more preferably both are substituted 2-thienyl and especially both are 2-(5-methyl)-thienyl.

These compounds may be preferably used as olefin polymerization catalyst components to produce highly stereoregular olefin polymers. Also these metallocene compounds may be preferably used as olefin polymerization catalyst components to produce high molecular weight and highly stereoregular olefin polymers, with high polymerization activity. These metallocene compounds may also be preferably used as olefin polymerization catalyst components for copolymerization of propylene and olefin other than propylene, with virtually no or less reduction in molecular weight of the resulting propylene/olefin copolymers even when the content of the olefin unit other than propylene is increasing, but instead allowing production of propylene/olefin copolymers of even high molecular weight comparable to propylene homopolymers produced under the same conditions. Such metallocene compounds may also be especially preferably used as olefin polymerization catalyst components for copolymerization of propylene and olefin other than propylene, to produce random copolymers or random block copolymers with few soluble components in o-dichlorobenzene.

As such metallocene compounds there may be mentioned, specifically, dimethylsilylenebis(2-methyl-4-(2-furyl)-4-hydroazulenyl)zirconium dichloride, dimethylsilylenebis(2-methyl-4-(2-(5-methyl)-furyl)-4-hydroazulenyl)zirconium dichloride, dimethylsilylenebis(2-ethyl-4-(2-(5-methyl)-furyl)-4-hydroazulenyl)zirconium dichloride, dimethylgermylenebis(2-methyl-4-(2-(5-methyl)-furyl)-4-hydroazulenyl)zirconium dichloride, dimethylsilylenebis(2-methyl-4-(2-(5-phenyl)-furyl)-4-hydroazulenyl)zirconium dichloride, dimethylsilylenebis(2-methyl-4-(2-(5-t-butyl)-furyl)-4-hydroazulenyl)zirconium dichloride, dimethylsilylenebis(2-methyl-4-(2-(5-trimethylsilyl)-furyl)-4-hydroazulenyl)zirconium dichloride, dimethylsilylenebis(2-methyl-4-(2-benzofuryl)-4-hydroazulenyl)zirconium dichloride, dimethylsilylenebis(2-methyl-4-(2-(4,5-dimethyl)-furyl)-4-hydroazulenyl)zirconium dichloride, dimethylsilylenebis(2-methyl-4-(2-thienyl)-4-hydroazulenyl)zirconium dichloride, dimethylsilylenebis(2-methyl-4-(2-(5-methyl)-thienyl)-4-hydroazulenyl)zirconium dichloride, dimethylsilylenebis(2-methyl-4-(2-(5-phenyl)-thienyl)-4-hydroazulenyl)zirconium dichloride, dimethylsilylenebis(2-methyl-4-(2-(5-t-butyl)-thienyl)-4-hydroazulenyl)zirconium dichloride, dimethylsilylenebis(2-methyl-4-(2-(5-trimethylsilyl)-thienyl)-4-hydroazulenyl)zirconium dichloride, dimethylsilylenebis(2-methyl-4-(2-benzothienyl)-4-hydroazulenyl)zirconium dichloride, dimethylsilylenebis(2-methyl-4-(2-(4,5-dimethyl)-thienyl)-4-hydroazulenyl)zirconium dichloride or dimethylsilylenebis(2-methyl-4-(2-furfuryl)-4-hydroazulenyl)zirconium dichloride.

Preferred among these are dimethylsilylenebis(2-methyl-4-(2-(5-methyl)-furyl)-4-hydroazulenyl)zirconium dichloride, dimethylsilylenebis(2-methyl-4-(2-(5-methyl)-thienyl)-4-hydroazulenyl)zirconium dichloride, dimethylsilylenebis(2-methyl-4-(2-(5-phenyl)-thienyl)-4-hydroazulenyl)zirconium dichloride, dimethylsilylenebis(2-methyl-4-(2-(5-t-butyl)-thienyl)-4-hydroazulenyl)zirconium dichloride or dimethylsilylenebis(2-methyl-4-(2-benzothienyl)-4-hydroazulenyl)zirconium dichloride.

Most preferred are dimethylsilylenebis(2-methyl-4-(2-(5-methyl)-thienyl)-4-hydroazulenyl)zirconium dichloride, dimethylsilylenebis(2-methyl-4-(2-(5-phenyl)-thienyl)-4-hydroazulenyl)zirconium dichloride, dimethylsilylenebis(2-methyl-4-(2-(5-t-butyl)-thienyl)-4-hydroazulenyl)zirconium dichloride or dimethylsilylenebis(2-methyl-4-(2-benzothienyl)-4-hydroazulenyl)zirconium dichloride.

Another preferred embodiment among the metallocene compounds represented by general formula (3) are metallocene compounds wherein each $R_3$ and each $R_4$ is independently a 2-furyl group, substituted 2-furyl group, 2-thienyl group, substituted 2-thienyl group, 2-furfuryl group or substituted 2-furfuryl group, preferably both are substituted 2-furyl groups, and even more preferably both are 2-(5-methyl)-furyl, or each $R_3$ is independently a 2-furyl group or substituted 2-furyl group and each $R_4$ is independently a 2-thienyl group or substituted 2-thienyl group.

These metallocene compounds may be preferably used as olefin polymerization catalyst components to produce high molecular weight and highly stereoregular olefin polymers, with high polymerization activity. These metallocene compounds may also be especially preferably used as olefin polymerization catalyst components for copolymerization of propylene and olefin other than propylene, with virtually no or less reduction in molecular weight of the resulting propylene/olefin copolymers even when the content of the olefin unit other than propylene is increasing, but instead allowing production of propylene/olefin copolymers of even high molecular weight comparable to propylene homopolymers produced under the same conditions. Such metallocene compounds may also be especially preferably used as olefin polymerization catalyst components for copolymerization of propylene and olefin other than propylene, to produce random copolymers or random block copolymers with few soluble components in o-dichlorobenzene.

Specific examples of such metallocene compounds include dimethylsilylenebis(2-(2-furyl)-4-(2-furyl)-4-hydroazulenyl)zirconium dichloride, dimethylsilylenebis(2-(2-furyl)-4-(2-(5-methyl)-furyl)-4-hydroazulenyl)zirconium dichloride, dimethylsilylenebis(2-(2-furyl)-4-(2-(5-phenyl)-furyl)-4-hydroazulenyl)zirconium dichloride, dimethylsilylenebis(2-(2-furyl)-4-(2-(5-t-butyl)-furyl)-4-hydroazulenyl)zirconium dichloride, dimethylsilylenebis(2-(2-furyl)-4-(2-(5-trimethylsilyl)-furyl)-4-hydroazulenyl)zirconium dichloride, dimethylsilylenebis(2-(2-furyl)-4-(2-benzofuryl),-4-hydroazulenyl)zirconium dichloride, dimethylsilylenebis(2-(2-furyl)-4-(2-(4,5-dimethyl)-furyl)-4-hydroazulenyl)zirconium dichloride, dimethylsilylenebis(2-(2-(5-methyl)-furyl)-4-(2-furyl)-4-hydroazulenyl)zirconium dichloride, dimethylsilylenebis(2-(2-(5-methyl)-furyl)-4-(2-(5-methyl)-furyl)-4-hydroazulenyl)zirconium dichloride, dimethylsilylenebis(2-(2-(5-methyl)-furyl)-4-(2-(5-phenyl)-furyl)-4-hydroazulenyl)zirconium dichloride, dimethylsilylenebis(2-(2-(5-methyl)-furyl)-4-(2-(5-t-butyl)-furyl)-4-hydroazulenyl)zirconium dichloride, dimethylsilylenebis(2-(2-(5-methyl)-furyl)-4-(2-(5-trimethylsilyl)-furyl)-4-hydroazulenyl)zirconium dichloride, dimethylsilylenebis(2-(2-(5-methyl)-furyl)-4-(2-benzofuryl)-4-hydroazulenyl)zirconium dichloride, dimethylsilylenebis(2-(2-(5-methyl)-furyl)-4-(2-(4,5-dimethyl)-furyl)-4-hydroazulenyl)zirconium dichloride, dimethylsilylenebis(2-(2-(5-methyl)-furyl)-4-(2-thienyl)-4-hydroazulenyl)zirconium dichloride, dimethylsilylenebis(2-(2-(5-methyl)-thienyl)-4-(2-(5-methyl)-furyl)-4-hydroazulenyl)zirconium dichloride, dimethylsilylenebis(2-(2-(5-methyl)-furyl)-4-(2-(5-phenyl)-thienyl)-4-hydroazulenyl)zirconium dichloride, dimethylsilylenebis(2-(2-(5-methyl)-thienyl)-4-(2-(5-t-butyl)-furyl)-4-hydroazulenyl)zirconium dichloride, dimethylsilylenebis(2-(2-(5-methyl)-furyl)-4-(2-(5-trimethylsilyl)-thienyl)-4-hydroazulenyl)zirconium dichloride, dimethylsilylenebis(2-(2-(5-methyl)-furyl)-4-(2-benzothienyl)-4-hydroazulenyl)zirconium dichloride and dimethylsilylenebis(2-(2-(5-methyl)-furyl)-4-(2-(4,5-dimethyl)-thienyl)-4-hydroazulenyl)zirconium dichloride.

Preferred among these are dimethylsilylenebis(2-(2-(5-methyl)-furyl)-4-(2-(5-methyl)-furyl)-4-hydroazulenyl)zirconium dichloride, dimethylsilylenebis(2-(2-(5-methyl)-furyl)-4-(2-(5-methyl)-thienyl)-4-hydroazulenyl)zirconium dichloride, dimethylsilylenebis(2-(2-(5-methyl)-furyl)-4-(2-(5-phenyl)-thienyl)-4-hydroazulenyl)zirconium dichloride or dimethylsilylenebis(2-(2-(5-methyl)-furyl)-4-(2-benzothienyl)-4-hydroazulenyl)zirconium dichloride.

Another preferred embodiment among the metallocene compounds of the invention represented by general formula (1) above are metallocene compounds represented by the following general formula (4).

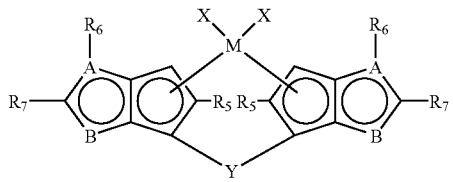

(4)

wherein each $R_5$ independently represents a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group. The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

Preferred as $R_5$ are $C_1$–$C_6$ alkyl, 2-furyl or substituted 2-furyl groups. More preferred are methyl, ethyl, isopropyl, 2-furyl or substituted 2-furyl. Most preferred are methyl or substituted 2-furyl. Both $R_5$ are preferably the same.

Each $R_6$ independently represents a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group. The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

Preferred as $R_6$ are $C_6$–$C_{16}$ aryl, halogen-containing aryl, 2-furyl or substituted 2-furyl groups. Even more preferred are $C_6$–$C_{16}$ aryl or substituted 2-furyl. Both $R_6$ are preferably the same.

Each $R_7$ independently represents hydrogen, a $C_1$–$C_6$ alkyl group, $C_1$–$C_6$ halogen-containing alkyl group, $C_1$–$C_6$ silicon-containing alkyl group, $C_6$–$C_{16}$ aryl group, $C_6$–$C_{16}$ halogen-containing aryl group, 2-furyl group, substituted 2-furyl group, 2-thienyl group, substituted 2-thienyl group, 2-furfuryl group or substituted 2-furfuryl group. The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

Preferred as $R_7$ are hydrogen or $C_1$–$C_6$ alkyl groups. More preferred are $C_1$–$C_6$ alkyl groups, and especially preferred is methyl. Both $R_7$ are preferably the same.

At least one substituent among each $R_5$, each $R_6$ and each $R_7$ is a 2-furyl group, substituted 2-furyl group, 2-thienyl group, substituted 2-thienyl group, 2-furfuryl group or substituted 2-furfuryl group.

Each A independently represents a carbon atom or an atom of Group 15 of the Periodic Table. A is preferably a carbon, nitrogen or phosphorus atom, and more preferably a carbon or nitrogen atom. Both A atoms are preferably the same.

Each B independently represents a carbon atom or an atom of Group 16 of the Periodic Table. B is preferably a carbon, oxygen or sulfur atom, and more preferably a carbon or sulfur atom. Both B atoms are preferably the same.

A and B may not both be carbon atoms. However, preferably either one of A and B is a carbon atom. When B is a carbon atom, B may have a substituent bonded to it. As substituents there may be used $C_1$–$C_6$ alkyl, $C_1$–$C_6$ silicon-containing hydrocarbon, $C_1$–$C_6$ halogen-containing hydrocarbon, $C_6$–$C_{16}$ aryl, $C_6$–$C_{16}$ halogen-containing aryl, 2-furyl, substituted 2-furyl, 2-thienyl, substituted 2-thienyl, 2-furfuryl or substituted 2-furfuryl groups, so long as the effect of the invention is not hindered. The $C_6$–$C_{16}$ aryl group may, if desired, be substituted with one or more $C_1$–$C_6$ hydrocarbon, silicon-containing hydrocarbon or halogen-containing hydrocarbon groups, or it may be substituted with an alkoxy, dialkyl-substituted amino, amino, 2-furyl, substituted 2-furyl, 2-thienyl, substituted 2-thienyl, 2-furfuryl or substituted 2-furfuryl group.

One of the preferred embodiment among the metallocene compounds of general formula (4) are metallocene compounds wherein each $R_5$ is independently 2-furyl, substituted 2-furyl, 2-thienyl, substituted 2-thienyl, 2-furfuryl or substituted 2-furfuryl, and preferably both are substituted 2-furyl and especially 2-(5-methyl)-furyl; each $R_6$ is independently $C_1$–$C_6$ alkyl, $C_1$–$C_6$ halogen-containing alkyl, $C_1$–$C_6$ silicon-containing alkyl, $C_6$–$C_{16}$ aryl, $C_6$–$C_{16}$ halogen-containing aryl, preferably $C_6$–$C_{16}$ aryl, $C_6$–$C_{16}$ halogen-containing aryl, more preferably phenyl, chlorophenyl, naphthyl or phenanthryl, and most preferably both are phenyl. These compounds may be preferably used as olefin polymerization catalyst components to produce high molecular weight and highly stereoregular olefin polymers, with high polymerization activity.

Specific examples of such compounds include those listed below as general formulas (5) to (8). In the formulas, "Me" represents methyl and "Ph" represents phenyl.

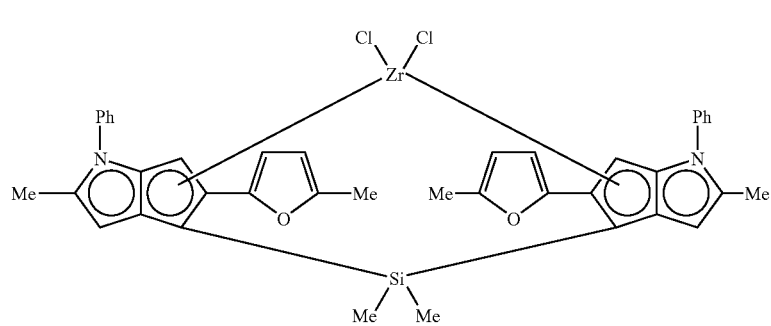

(5)

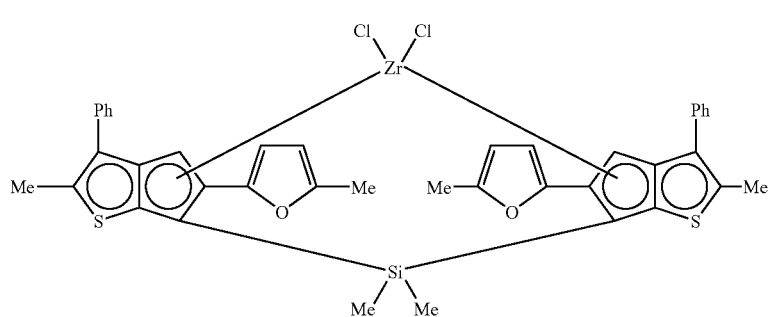

(6)

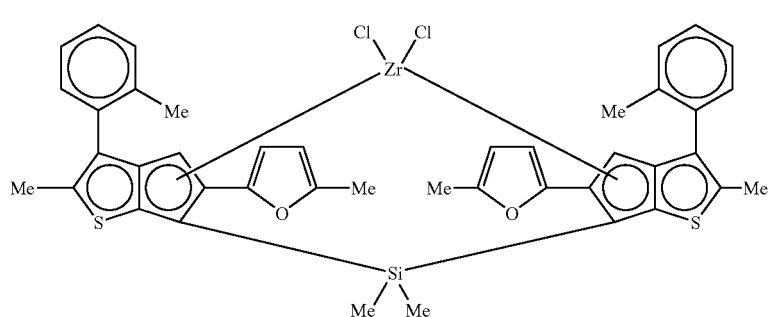

(7)

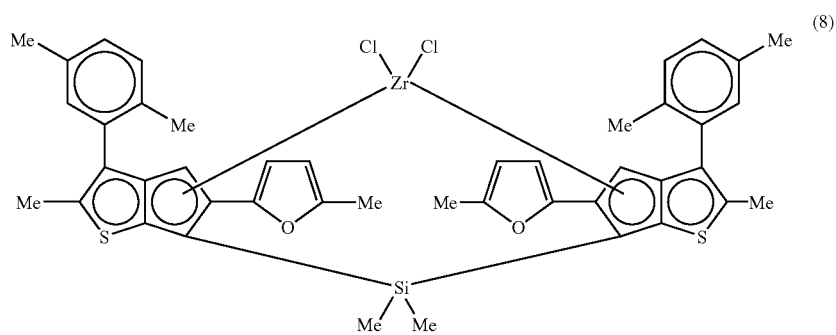

(8)

Another preferred embodiment among the metallocene compounds of general formula (4) are metallocene compounds wherein each $R_5$ independently represents a $C_1$–$C_6$ alkyl group, $C_1$–$C_6$ halogen-containing alkyl group, $C_1$–$C_6$ silicon-containing alkyl group, $C_6$–$C_{16}$ aryl group or $C_6$–$C_{16}$ halogen-containing aryl group, preferably a $C_1$–$C_6$ alkyl group, more preferably methyl or ethyl, and most preferably both are methyl; each $R_6$ independently represents a 2-furyl group, substituted 2-furyl group, 2-thienyl group, substituted 2-thienyl group, 2-furfuryl group or substituted 2-furfuryl group, preferably both are substituted 2-furyl groups, and most preferably both are 2-(5-methyl)-furyl. These compounds may be preferably used as olefin polymerization catalyst components to produce high molecular weight olefin polymers, with high polymerization activity.

Specific examples of such compounds include those listed below as general formulas (9) to (12). In the formulas, "Me" represents methyl.

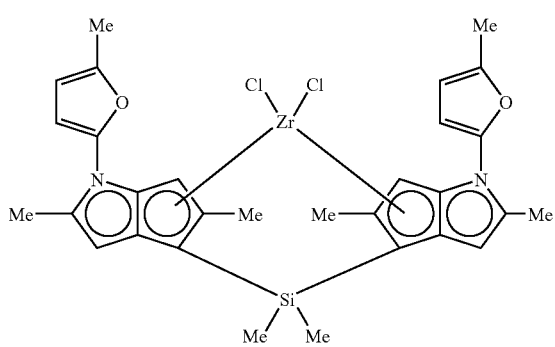

(9)

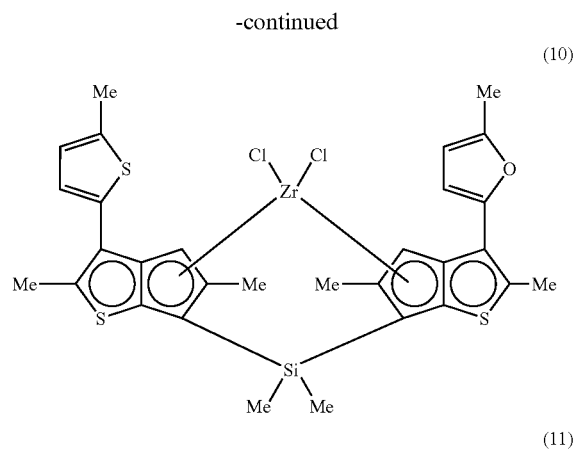

(10)

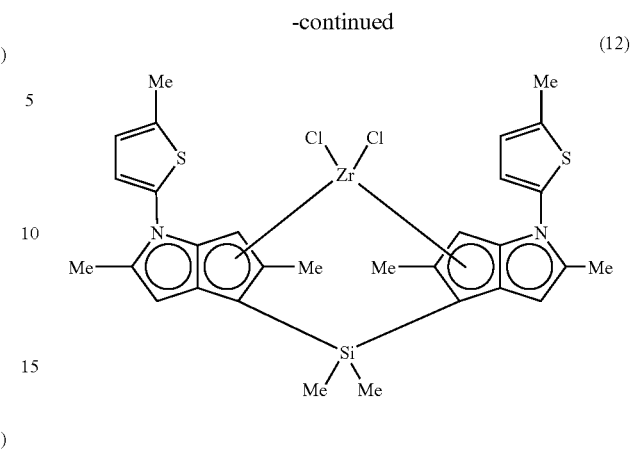

(12)

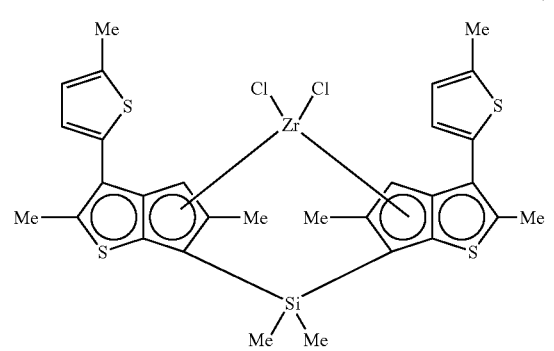

(11)

Another preferred embodiment among the metallocene compounds of general formula (4) are metallocene compounds wherein each $R_5$ and each $R_6$ is independently a 2-furyl group, substituted 2-furyl group, 2-thienyl group, substituted 2-thienyl group, 2-furfuryl group or substituted 2-furfuryl group, preferably both are substituted 2-furyl groups, and more preferably both are 2-(5-methyl)-furyl. These compounds may be preferably used as olefin polymerization catalyst components to produce high molecular weight and highly stereoregular olefin polymers, with high polymerization activity.

Specific examples of such compounds include those listed below as general formulas (13) and (14). In the formulas, "Me" represents methyl.

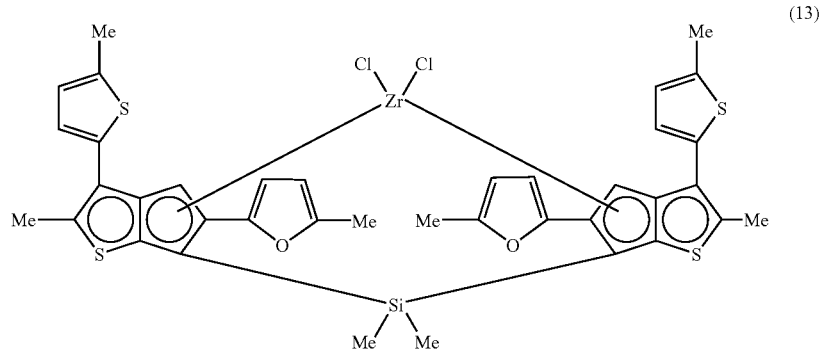

(13)

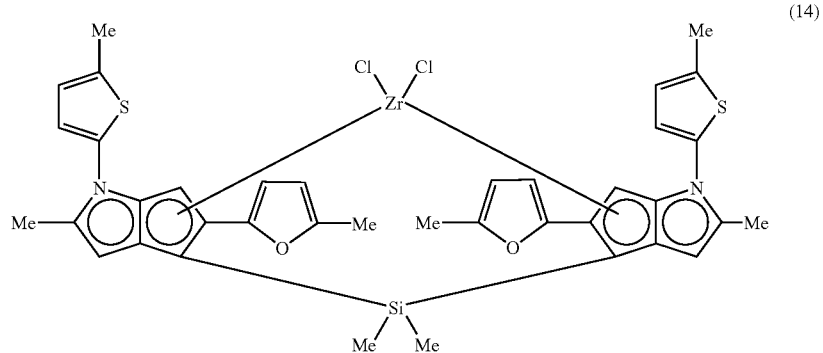

(14)

Examples of metallocene compounds of the invention also include metallocene compounds represented by the following general formulas (15) to (17), which are compounds of general formula (1) wherein the K and L are different fused rings each other. The definitions of the reference letters used in general formulas (15) to (17) are the same as those used in general formulas (1) to (4).

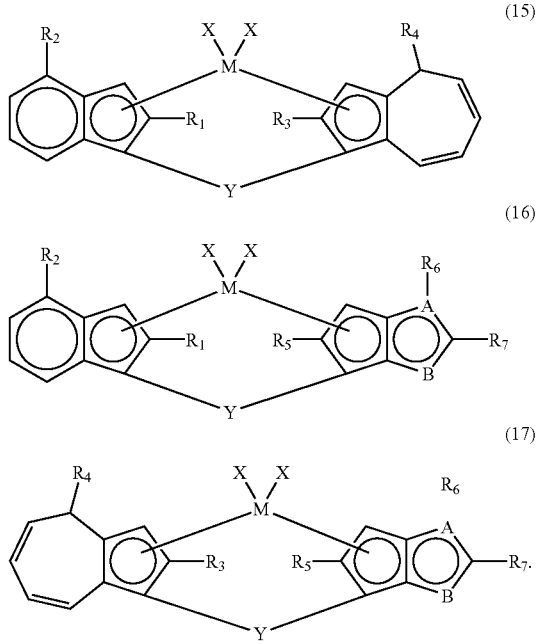

Most preferred as metallocene compounds of the invention are the metallocene compounds represented by general formula (3), wherein each $R_3$ is independently $C_1$–$C_6$ alkyl, $C_1$–$C_6$ halogen-containing alkyl, $C_6$–$C_{16}$ aryl, $C_6$–$C_{16}$ halogen-containing aryl, more preferably $C_1$–$C_6$ alkyl, even more preferably methyl or ethyl and especially both are methyl; and each $R_4$ is independently 2-furyl, substituted 2-furyl, 2-thienyl, substituted 2-thienyl, 2-furfuryl or substituted 2-furfuryl, preferably 2-furyl, substituted 2-furyl, 2-thienyl or substituted 2-thienyl, and more preferably both are substituted 2-thienyl and especially both are 2-(5-methyl)-thienyl.

According to the invention, there is no particular restriction that the metallocene compounds must be in the racemic form or meso form, but the racemic form is preferred for achieving the desired effect of the invention when used as an olefin polymerization catalyst component.

The characteristic of the metallocene compounds of the invention is having specific positions, however, the metallocene compounds of the invention may be produced using publicly known starting materials and by publicly known process.

The metallocene compounds of the invention may be used in combination with other components as olefin polymerization catalysts for production of olefin polymers. Catalysts containing the metallocene compounds of the invention may be largely classified into the following categories (1) to (3).

(1) Olefin polymerization catalysts comprising the aforementioned metallocene compounds (hereinafter also referred to as "component (A)"), an activating compound (hereinafter also referred to as "component (B)") and, if desired, an organic aluminum compound (hereinafter referred to as "component (D)") (the catalysts will hereinafter also be referred to as "metallocene homogeneous catalysts").

(2) Olefin polymerization catalysts comprising a supported metallocene catalyst characterized by being produced using component (A), component (B), a fine particulate support (hereinafter also referred to as "component (C)") and, if desired, component (D) (the supported metallocene catalyst will hereinafter also be referred to as "supported metallocene catalyst I") with an organic aluminum compound (hereinafter also referred to as "component (D')").

(3) Olefin polymerization catalysts comprising a supported metallocene catalyst characterized by being produced using component (A), an ion-exchangeable layer compound or an inorganic silicate (hereinafter also referred to as "component (E)") and, if desired, component (D) (the wherein $R^3$ is a hydrocarbon group of 1–6 carbons. Specifically there may be mentioned alkyl groups such as methyl, ethyl, propyl, butyl, isobutyl, pentyl or hexyl; alkenyl groups such as allyl, 2-methylallyl, propenyl, isopropenyl, 2-methyl-1-propenyl or butenyl; cycloalkyl groups such as cyclopropyl, cyclobutyl, cyclopentyl or cyclohexyl; and aryl groups. Among these, hydrocarbon groups of 1–4 carbons are preferred, with alkyl groups being the most preferred hydrocarbons. Each $R^3$ may be the same or different. Letter "q" is an integer of 4–30, preferably 6–30 and more preferably 8–30.

The aluminoxane may be prepared under publicly known conditions. The following may be mentioned as examples of specific methods.

(1) A method of directly reacting trialkylaluminum and water in an organic solvent such as toluene or ether;

(2) A method of reacting trialkylaluminum with a salt containing water of crystallization such as copper sulfate hydrate or aluminum sulfate hydrate or the like;

(3) A method of reacting trialkylaluminum with water impregnated in silica gel or the like;

(4) A method of directly reacting a mixture of trimethylaluminum and triisobutylaluminum with water in an organic solvent such as toluene or ether;

(5) A method of reacting a mixture of trimethylaluminum and triisobutylaluminum with a salt supported metallocene catalyst will hereinafter also be referred to as "supported metallocene catalyst II") with component (D').

Of the supported metallocene catalysts I or II described in (2) and (3) above, the supported metallocene catalyst I described in (2) above is preferably used for production of an olefin polymer according to the invention. The supported metallocene catalyst I is particularly preferred when using a metallocene compound of general formula (3) as the metallocene compound (A).

Component (B) is preferably an organic aluminoxy compound or a compound which reacts with component (A) to form an ion pair. As organic aluminoxy compounds there may be used the aluminoxanes represented by the following general formulas (18) or (19).

containing water of crystallization such as copper sulfate hydrate or aluminum sulfate hydrate or the like;

(6) A method of reacting triisobutylaluminum with water impregnated in silica gel or the like, and then further reacting the product with trimethylaluminum.

As compounds that form ion pairs by reaction with component (A) there may be mentioned the Lewis acids, ionic compounds, borane compounds or carborane compounds described in Japanese Patent Kohyo H1-501950, Japanese Patent Kohyo H1-502036, Japanese Patent Kokai H3-179005, Japanese Patent Kokai H3-179006, Japanese Patent Kokai H3-207704, WO92/00333, U.S. Pat. No. 5,064,802, WO93/03067, JP-A-4-309508, JP-A-4-353502, JP-A-5-331232, WO00/20426, Chem. Rev. 100, 1391–1434 (2000) and others.

Preferred Lewis acids are Lewis acids containing boron atoms, and as non-limitative examples there may be mentioned trifluoroboron, triphenylboron, tris(4-fluorophenyl) boron, tris(3,5-fluorophenyl)boron, tris(4-fluoromethylphenyl)boron, tris(p-tolyl)boron, tris(o-tolyl)boron, tris(3,5-dimethylphenyl)boron, tris(pentafluorophenyl)boron, and the like. Particularly preferred among these is tris(pentafluorophenyl)boron.

An ionic compound is a salt comprising a cationic compound and an anionic compound. The anionic compound has the function of reacting with the metallocene compound and of cationizing the metallocene compound and forming an ion pair, thereby stabilizing the transition metal cation species. Such anionic compounds include organic boron compound anions, organic arsenic compound anions, organic aluminum compound anions and the like, among which those which are relatively bulky and stabilize transition metal cations are preferred. As cationic compounds there may be mentioned metal cations, organic metal cations, carbonium cations, tripium cations, oxonium cations, sulfonium cations, phosphonium cations, ammonium cations and the like. Specific ones include triphenylcarbenium cation, tributylammonium cation, N,N-dimethylammonium cation and ferrocenium cation.

As ionic compounds there may be suitably used salts containing boron compounds, as anionic compounds. Specifically there may be mentioned the following trialkyl-substituted ammonium salts: triethylammonium tetra(phenyl)boron, tripropylammonium tetra(phenyl)boron, tri(n-butyl)ammonium tetra(phenyl)boron, trimethylammonium (p-tolyl)boron, trimethylammonium(o-tolyl)boron, tributylammonium tetra(pentafluorophenyl)boron, tripropylammonium tetra(o,p-dimethylphenyl)boron, tributylammonium tetra(m,m-dimethylphenyl)boron, tributylammonium tetra(p-trifluoromethylphenyl)boron, tri(n-butyl)ammonium tetra(o-tolyl)boron and tri(n-butyl)ammonium tetra(4-fluorophenyl)boron.

As N,N-dialkylanilinium salts there may be mentioned N,N-dimethylanilinium tetra(phenyl)boron, N,N-diethylanilinium tetra(phenyl)boron and N,N,N-2,4,6 -pentamethylanilinium(phenyl)boron, as examples of dialkylammonium salts there may be mentioned di(n-propyl)ammonium tetra (pentafluorophenyl)boron, dicyclohexylammonium tetra(pentafluorophenyl)boron, and as examples of trialkylphosphonium salts and triarylphosphonium salts there may be mentioned trimethylphosphonium tetra(phenyl)boron, tri (methylphenyl)phosphonium tetra(phenyl)boron and tri (dimethylphenyl)phosphonium tetra(phenyl)boron.

As ionic compounds containing boron atoms according to the invention there may be further mentioned triphenylcarbenium tetrakis(pentafluorophenyl)borate, N,N-dimethylanilinium tetrakis(pentafluorophenyl)borate and ferrocenium tetra(pentafluorophenyl)borate.

Aluminoxanes are particularly preferred among these activating compounds.

Component (C) used as a starting material for the supported metallocene catalyst I used for production of an olefin polymer according to the invention is an inorganic support or organic support, and a granular or spherical inorganic fine particulate support or organic fine particulate support is used having a particle size of 1–500 μm, preferably 5–300 μm and more preferably 10–150 μm.

An inorganic fine particulate support has a specific surface area in the range of 50–1000 $m^2/g$ and preferably 100–700 $m^2/g$, and a pore volume in the range of 0.3–2.5 $m^3/g$.

As inorganic fine particulate supports there are preferred metal oxides, for example, $SiO_2$, $Al_2O_3$, MgO, $TiO_2$, ZnO and their mixtures or compound oxides, with supports composed mainly of $SiO_2$ or $Al_2O_3$ being particularly preferred. As inorganic compounds there may be mentioned more specifically $SiO_2$, $Al_2O_3$, MgO, $SiO_2$—$Al_2O_3$, $SiO_2$—MgO, $SiO_2$—$TiO_2$, $SiO_2$—$Al_2O_3$—MgO, or chromium compound supported $SiO_2$ and the like, among which $SiO_2$ is particularly preferred.

These inorganic fine particulate supports are usually used after calcined at 100–1000° C., preferably 300–900° C. and most preferably 400–900° C. The surface-adsorbed water on the calcined inorganic fine particulate support is no greater than 0.1 wt % and preferably no greater than 0.01 wt %, while the surface-hydroxyl content is at least 1.0 wt %, preferably 1.5–4.0 wt % and more preferably 2.0–3.5 wt %. The inorganic fine particles may, before use, be catalyst-treated with an organic aluminum compound and/or a halogen-containing silicon compound, or catalyst-treated with an acid such as chromium (II) nitrate.

Examples of fine particulate organic supports include fine particulate organic polymers, for example, fine particulate polymers of polyolefins such as polyethylene, polypropylene, poly-1-butene and poly-4-methyl-1-pentene, or fine particulate polymers of polystyrene or the like.

As the organic aluminum compound of component (D) there may be suitably used compounds represented by the general formula $AlR^4{}_sR^5{}_tX_{3-(s+t)}$. In this formula, $R^4$ and $R^5$ each independently represent a hydrocarbon group such as alkyl group, cycloalkyl group, aryl group, etc. of 1–10 carbons, an alkoxy group, a fluorine atom, methyl, or an optionally substituted phenyl group such as trifluorophenyl. X represents a halogen atom, and s and t represent any integers which satisfy the inequality $0<s+t\leq 3$.

Preferred examples of the aforementioned organic aluminum compound include trialkylaluminum such as trimethylaluminum, triethylaluminum, triisopropylaluminum, triisobutylaluminum, tri-n-butylaluminum, tri-n-hexylaluminum and tri-n-octylaluminum, dialkylaluminum halides such as dimethylaluminum chloride, dimethylaluminum bromide, diethylaluminum chloride and diisopropylaluminum chloride, alkylaluminum sesquihalides such as methylaluminum sesquichloride, ethylaluminum sesquichloride, ethylaluminum sesquibromide and isopropylaluminum sesquichloride, as well as mixtures of two or more thereof. Trialkylaluminum are more preferred, with triethylaluminum or triisobutylaluminum being even more preferred.

Examples of component (E) to be used for production of the supported metallocene catalyst II include ion-exchangeable layer compounds, or inorganic silicates. The term "ion-exchangeable layer compounds" used throughout the present application does not include silicates.

As ion-exchangeable layer compounds there may be mentioned ion crystalline compounds having a layer crystalline structure, such as hexagonal close-packed types, antimony types, $CdCl_2$ types and $CdI_2$ types, specific examples of which include crystalline acidic salts of polyvalent metals, such as α-$Zr(HAsO_4)_2 \cdot H_2O$, α-$Zr(HPO_4)_2$, α-$Zr(KPO_4)_2 \cdot 3H_2O$, α-$Ti(HPO_4)_2$; α-$Ti(HAsO_4)_2 \cdot H_2O$, α-Sn(HPO$_4$)$_2$.H$_2$O, γ-Zr(HPO$_4$)$_2$, γ-Ti(HPO$_4$)$_2$, γ-Ti(NH$_4$PO$_4$)$_2$.H$_2$O, and the like.

These ion-exchangeable layer compounds may be used after salt treatment and/or acid treatment if necessary. An ion-exchangeable layer compound subjected to neither salt treatment nor acid treatment adopts a crystal structure wherein the surfaces composed of ionic bonds, etc. build up in a parallel fashion with weak binding force, and allows exchange of the ions present.

As the aforementioned inorganic silicates there may be mentioned clays, clay minerals, zeolite, diatomaceous earth and the like. These may be used as synthetic products, or as the naturally occurring minerals. Specific examples of clays and clay minerals include allophane types such as allophane, kaolin types such as dickite, nacrite, kaolinite or anauxite, halloysite types such as metahalloysite or halloysite, serpentine types such as chrysotile, lizardite or antigorite, smectite types such as montmorillonite, sauconite, beidellite, nontronite, saponite or hectorite, vermiculite minerals such as vermiculite, mica minerals such as illite, sericite or glauconite, attapulgite, sepiolite, palygorskite, bentonite, kibushi clay, gairome clay, hisingerite, pyroferrite, chlorite, and the like. These may also form mixed layers. As artificial synthetic minerals there may be mentioned synthetic mica, synthetic hectorite, synthetic saponite and synthetic tainiolite.

Preferred among these inorganic silicates are kaolin types, halloysite types, serpentine types, smectite types, vermiculite minerals, micas, synthetic mica, synthetic hectorite, synthetic saponite and synthetic tainiolite, with smectite, vermiculite minerals, synthetic mica, synthetic smectite, synthetic saponite and synthetic tainiolite being more preferred. These may be used directly without any particular processing, or they may be used after processing with a ball mill, sieve or the like. They may also be used either alone or in mixtures of two or more types.

These inorganic silicates, if necessary, may have their solid acid strength altered by salt treatment and/or acid treatment. Also, with salt treatment, the surface area or interlayer distance may be altered by forming ion complexes, molecular complexes, organic derivatives or the like. That is, by utilizing ion-exchange properties to replace the interlayer ion-exchangeable ions with large bulky ions, it is possible to obtain a laminar substance with increased interlayer regions.

Component (E) may be used without treatment, but the ion-exchangeable metal cation is preferably ion-exchanged with the below-mentioned salt- and/or acid-dissociated cations.

A salt used for the ion-exchange is a compound comprising a cation with at least one type of atom selected from the group consisting of Group 1–14 atoms, and preferably it is a compound comprising a cation with at least one type of atom selected from the group consisting of Group 1–14 atoms and an anion derived from at least one atom or atomic group selected from the group consisting of halogen atoms, inorganic acids and organic acids. More preferably, it is a compound comprising a cation with at least one atom selected from the group consisting of Group 2–14 atoms and at least one anion selected from the group consisting of Cl, Br, I, F, PO$_4$, SO$_4$, NO$_3$, CO$_3$, C$_2$O$_4$, ClO$_3$, ClO$_4$, OOCCH$_3$, CH$_3$COCHCOCH$_3$, OCl$_2$, O(NO$_3$)$_2$, O(ClO$_4$)$_2$, O(SO$_4$), OH, O$_2$Cl$_2$, OCl$_3$, OOCH, OOCCH$_2$CH$_3$, C$_2$H$_4$O$_4$ and C$_6$H$_5$O$_7$. Two or more of these salts may also be used in combination.

An acid used for the ion-exchange is preferably selected from among hydrochloric acid, sulfuric acid, nitric acid, acetic acid and oxalic acid, and these may be used together in combinations of two or more. Methods of combining salt treatment and acid treatment include methods of carrying out acid treatment after salt treatment, methods of carrying out salt treatment after acid treatment, methods of simultaneously carrying out salt treatment and acid treatment, and methods of simultaneously carrying out salt treatment and acid treatment after salt treatment. The acid treatment has an effect of eluting a portion of cations such as Al, Fe, Mg and Li in the crystal structure, in addition to its effect of ion-exchange and surface impurity removal.

There are no particular restrictions on the treatment conditions with the salt and acid. Usually, however, preferably the base or acid concentration is 0.1–30 wt %, the treatment conditions are selected so that the temperature is in a range of from room temperature to the boiling point of the solvent used, the treatment time is from 5 minutes to 24 hours and at least part of the compound being treated elutes. The salt and acid are generally used in aqueous solution.

When carrying out such salt treatment and/or acid treatment, pulverization or granulation may be carried out for shape control either before, during or after the treatment. Other chemical treatment such as alkali treatment, organic compound treatment or organic metal treatment may also be performed. Preferably the component (E) obtained in this manner has a volume of at least 0.1 cc/g, and especially 0.3–5 cc/g, of pores with a radius of 20 Å or greater as measured by the mercury injection method. When treated in aqueous solution, component (E) will contain adsorbed water and interlayer water. Adsorbed water is water adsorbed onto the surface of the ion-exchangeable layer compound or inorganic silicate, or to the crystal fracture surfaces, while interlayer water is water present between the crystal laminae.

Component (E) is preferably used after removal of this adsorbed water and interlayer water. The dewatering method is not particularly restricted, and a method such as heated dehydration, heated dehydration under a gas stream, heated dehydration under reduced pressure and azeotropic dehydration with an organic solvent may be used. The heating temperature is in a temperature range which allows no residue of adsorbed or interlayer water, which will normally be 100° C. or higher and preferably 150° C. or higher, but high temperature conditions which cause structural fracture are not preferred. The heating time is 0.5 hour or longer, and preferably 1 hour or longer. The weight reduction of component (E) after dehydration drying is preferably no greater than 3 wt % upon 2 hours of vacuum suction at a temperature of 200° C. and a pressure of 1 mmHg. According to the invention, when using component (E) prepared with a weight reduction of no greater than 3 wt %, it is preferably handled so as to maintain the same weight reduction state even upon contact with component (A) and component (D).

A process for production of supported metallocene catalysts I and II will now be described.

Supported metallocene catalyst I is obtained by reacting component (A), component (B), and component (D) if desired, in the presence of component (C). The order of adding component (A) and component (B) to component (C) may be any desired order. For example, component (A) dissolved in an appropriate hydrocarbon solvent may first be added to component (C), and then component (B) may be added thereto. Alternatively, component (B) and component (A) may be reacted in advance, and the product added to component (C). Also, component (B) may first be added to component (C) and then component (A) added thereto. The temperature during the reaction will normally be −20° C. to 200° C. and preferably 0° C. to 120° C., and the time required for the reaction will usually be in the range of 0.1 minute or longer and preferably from 1 to 200 minutes. The supported metallocene catalyst I obtained in this manner may be used after prepolymerization with a small amount of an olefin if necessary.

As olefins to be used for prepolymerization there may be mentioned ethylene, propylene, 1-butene, 1-hexene, 3-methyl-1-butene and 4-methyl-1-pentene, and two or more olefins may be used in admixture.

As a supported metallocene catalyst I that may be suitably used for production of olefin polymers according to the invention there may be mentioned a supported metallocene catalyst prepared by carrying out steps (a) to (c) below or a preactivated supported metallocene catalyst obtained by carrying out steps (a) to (d) below.

(a) A step of reacting metallocene compound (A) with an aluminoxane in an inert solvent to obtain a metallocene catalyst;

(b) A step of contacting the metallocene catalyst obtained in step (a) above with an inorganic fine particulate support in the presence of an inert solvent at a temperature of 85–150° C. to load the metallocene catalyst on the inorganic fine particulate support, to obtain a crude supported metallocene catalyst;

(c) A step of washing the slurry containing the crude supported metallocene catalyst obtained in step (b) above at least twice using an aliphatic hydrocarbon at a temperature of −50° C. to 50° C. to obtain a purified supported metallocene catalyst;

(d) A step of contacting the supported metallocene catalyst obtained in step (c) above with an olefin for prepolymerization of the olefin, and then loading the olefin prepolymer on the supported metallocene catalyst at 0.01–500 kg per kg of the supported metallocene catalyst, to obtain a preactivated supported metallocene catalyst.

In step (a), 10–1000 moles and preferably 20–500 moles of the aluminoxane in terms of aluminum atoms is reacted with one mole of the metallocene compound (A), in an inert solvent at a temperature in the range of −50° C. to 100° C. and preferably 0° C. to 50° C., for 1 minute to 10 hours and preferably 3 minutes to 5 hours, to produce a metallocene catalyst.

An inert solvent is preferably used to uniformly and efficiently promote the reaction. There are no particular restrictions on the amount of the inert solvent used, but it will usually be about 10–10,000 liters and preferably 10–1000 liters with respect to one mole of the metallocene compound (A).

As examples of inert solvents to be used there may be mentioned aromatic hydrocarbons such as benzene, toluene, xylene and cumene, aliphatic hydrocarbons such as butane, tetramethylbutane, pentane, ethylpentane, trimethylpentane, hexane, methylhexane, ethylhexane, dimethylhexane, heptane, methylheptane, octane, nonane, decane, hexadecane and octadecane, alicyclic hydrocarbons such as cyclopentane, methylcyclopentane, cyclohexane and cyclooctane, and halogenated hydrocarbons wherein the aforementioned aromatic hydrocarbons, aliphatic hydrocarbons or alicyclic hydrocarbons are substituted with halogens, as well as mixtures of these solvents. An ether such as ethyl ether and tetrahydrofuran may also be used as the inert solvent.

An aromatic hydrocarbon is preferred as the inert solvent. A commercially available aluminoxane solution solvent may be used directly, or other aromatic hydrocarbons may be added thereto for the reaction.

In step (b) which follows step (a), the metallocene catalyst obtained in step (a) and an inorganic fine particulate support are contacted in the presence of the inert solvent used as the reaction solvent in step (a) at a temperature of 85–150° C., to obtain a crude supported metallocene catalyst as a solid product having the metallocene catalyst supported on the inorganic fine particulate support. An additional inert solvent may be used if necessary in the contact reaction.

The proportion of the metallocene catalyst and inorganic fine particulate support in the crude supported metallocene catalyst is 1–1000 kg, and preferably 5–500 kg, of the inorganic fine particulate support with respect to one mole of the transition metal atom of the metallocene compound (A) portion in the reaction product of the metallocene compound (A) and the aluminoxane as the metallocene catalyst. The amount of the inert solvent used in step (b) is 10–10,000 liters, and preferably 10–1000 liters, with respect to one mole of the transition metal atom of the metallocene compound (A) portion in the reaction product of the metallocene compound (A) and the aluminoxane as the metallocene catalyst.

The contact between the metallocene catalyst and the inorganic fine particulate support is accomplished at a temperature of 85–150° C., preferably 90–130° C. and especially 95–120° C., for a period of 5 minutes to 100 hours and preferably 10 minutes to 50 hours. The temperature condition is an especially major factor, and by accomplishing the contact in the temperature range specified above, the obtained supported metallocene catalyst exhibits high polymerization activity, and using the catalyst for olefin polymerization results in olefin polymers with high bulk specific gravity and satisfactory particle properties.

In the subsequent step (c), the crude supported metallocene catalyst containing the inert solvent obtained in step (b) is washed at least twice using an aliphatic hydrocarbon at a temperature of −50° C. to 50° C. to obtain a purified supported metallocene catalyst.

The aliphatic hydrocarbon used for the washing may be any of the aliphatic hydrocarbons mentioned above for the inert solvent, or mixtures thereof. Preferred are n-hexane, isopentane and their mixtures.

As the washing method in step (c), for example, after completion of step (b), the inert solvent may be separated by filtration, centrifugation or decantation from the slurry comprising the inert solvent and crude supported metallocene catalyst, and then an aliphatic hydrocarbon may be used to wash the crude supported metallocene catalyst. Alternatively, after completion of step (b), an aliphatic hydrocarbon may first be added without separating the inert solvent from the slurry comprising the inert solvent and the crude metallocene catalyst, and then the mixture of the inert solvent and the aliphatic hydrocarbon may be separated by the same means described above, and the aliphatic hydrocarbon used to wash the crude supported metallocene catalyst. The washing method carried out in step (c) is more preferably the latter method.

The washing is repeated, using 1–500 liters and preferably 10–100 liters of the aliphatic hydrocarbon with respect to 1 kg of the inorganic fine particulate support used in step (b) for each washing, at a temperature of −50° C. to 50° C., preferably −30° C. to 40° C. and especially −30° C. to 30° C., until the metallocene catalyst no longer elutes into the aliphatic hydrocarbon after washing. Washing will be sufficient if repeated at least two times and usually four or more times, but this is not restrictive.

The washing temperature condition is a major factor, and washing within the temperature range specified above results in a supported metallocene catalyst with high polymerization activity, which when used for olefin polymerization results in olefin polymers with high bulk specific gravity and satisfactory particle properties.

A preactivated supported metallocene catalyst used according to the invention is obtained by, in step (d), contacting the supported metallocene catalyst obtained in step (c) above with an olefin for prepolymerization of the olefin, and then loading the olefin prepolymer on the supported metallocene catalyst at 0.01–500 kg per kg of the supported metallocene catalyst.

As the olefin prepolymer to be loaded on the preactivated supported metallocene catalyst there may be mentioned homopolymers of olefins of 2–20 carbons, for example, ethylene, propylene, 1-butene, 1-pentene, 4-methyl-1-pentene, 2-methyl-1-pentene, 1-hexene, 1-octene, 1-decene and 1-dodecene, as well as copolymers comprising combinations of two or more thereof. Particularly preferred are ethylene homopolymer, propylene homopolymer, ethylene/olefin copolymers of ethylene and olefins other than ethylene, composed mainly of ethylene, or propylene/olefin copolymers of propylene and olefins other than propylene, composed mainly of propylene. These olefin prepolymers have an intrinsic viscosity [η] in the range of 0.1–10 dl/g and preferably 0.2–7 dl/g as measured in decalin at 135° C. To obtain olefin polymers with high melt tension, however, the intrinsic viscosity [η] of the olefin prepolymer as measured in decalin at 135° C. is preferably in a range of greater than 10 dl/g and less than 100 dl/g, more preferably in a range of 15–80 dl/g and even more preferably in a range of 20–50 dl/g.

The preferred olefin prepolymerization method is a method in which the olefin to be prepolymerized is introduced into a slurry comprising the supported metallocene catalyst obtained in step (c) dispersed in an aliphatic hydrocarbon, and the olefin is contacted with the supported metallocene catalyst for prepolymerization. The slurry comprising the supported metallocene catalyst dispersed in the aliphatic hydrocarbon may be used without separating from the aliphatic hydrocarbon the catalyst obtained by the final step of washing in step (c), or else it may be used after separation and then redispersion in a similar aliphatic hydrocarbon.

The olefin prepolymerization may be carried out in a liquid phase with the prepolymerization olefin itself as the solvent or in a gas phase without using a solvent, but it is preferably carried out in the presence of an aliphatic hydrocarbon in order to control polymerization of a small amount of olefin and promote uniform prepolymerization.

The prepolymerization of the olefin is carried out in the aliphatic hydrocarbon by introducing 0.01–1000 kg and preferably 0.1–500 kg of the olefin into a slurry comprising 0.005–5 $m^3$ and preferably 0.01–1 $m^3$ of the aliphatic hydrocarbon with respect to 1 kg of the supported metallocene catalyst, and contacting the olefin therewith at a temperature of −50° C. to 100° C. and preferably 0° C. to 50° C. for a period of 1 minute to 50 hours and preferably 3 minutes to 20 hours.

While there is no particular need to newly add a cocatalyst, which is typically an organic aluminum compound such as a trialkylaluminum or an aluminoxane, for the olefin prepolymerization because the reaction product of the metallocene compound (A) and the aluminoxane suitable as the activating compound (B) is supported in the supported metallocene catalyst, one may still be added if desired. The amount of cocatalyst added is preferably kept within a range of no greater than 1000 moles and more preferably no greater than 500 moles in terms of aluminum atoms with respect to one mole of the transition metal atom of the metallocene compound (A) in the supported metallocene catalyst.

According to the invention, the olefin prepolymerization is carried out in the presence of hydrogen and the weight-average molecular weight (Mw) of the obtained olefin prepolymer is controlled to be in the range of 100,000 to 500,000 g/mole, to produce an olefin polymer with excellent particle properties.

As a process for production of a supported metallocene catalyst I which may be suitably used for production of an olefin polymer of the invention there may be mentioned, in addition to the process described above, a process in which the aluminoxane and inorganic fine particulate support are reacted and then the product is reacted with the metallocene compound (A). Using a catalyst obtained by this process allows production of olefin polymers with highly superior particle properties.

The supported metallocene catalyst II which may be used for the invention is prepared by contacting components (A), (E) and (D). The contacting method is not particularly restricted, and the following may be mentioned as examples.

(1) Contact of components (A) and (E).

(2) Contact of components (A) and (E), followed by addition of component (D).

(3) Contact of components (A) and (D), followed by addition of component (E).

(4) Contact of components (E) and (D), followed by addition of component (A).

(5) Simultaneous contact of components (A), (E) and (D).

The contact may be carried out during prepolymerization of the olefin or during polymerization of the olefin, instead of during the catalyst preparation. Either during or after contact of each of the components, the components may be copresent with or contacted with a solid of a polymer such as polyethylene or polypropylene or an inorganic oxide such as silica or alumina. Contact between the aforementioned components may be accomplished in an inert gas such as nitrogen or in an inert hydrocarbon solvent such as pentane, hexane, heptane, toluene or xylene. The contact is accomplished in a temperature range with a lower limit of −20° C. and an upper limit of the boiling point of the solvent, and most preferably is accomplished in a temperature range with a lower limit of room temperature and an upper limit of the boiling point of the solvent.

The amounts of each component used are as follows. Specifically, component (A) is usually used at $10^{-4}$ to 10 millimoles and preferably $10^{-3}$ to 5 millimoles and component (D) is usually used at 0.01–$10^4$ millimoles and preferably 0.1–100 millimoles, with respect to 1 g of component (E). The atomic ratio of the transition metal in component (A) and the aluminum in component (D) will usually be 0.01–$10^6$ and preferably 1:0.1–$10^5$. A catalyst prepared in this manner may be used without washing or after washing.

An additional component (D) may also be used if necessary. That is, when a catalyst is prepared using component (A) and/or component (E) with component (D), an additional component (D) may be added to the reaction system, separate from the catalyst preparation. In such cases, the amount of component (D) used will generally be selected to be 1:0–$10^4$ and preferably 1:1–$10^3$ as the atomic ratio of transitional metal atoms in the metallocene compound (a) of component (A) to aluminum atoms in component (D).

The supported metallocene catalyst II obtained in this manner, like the supported metallocene catalyst I, may be used for production of an olefin polymer of the invention after an olefin has been prepolymerized and the olefin prepolymer has been further loaded on the supported catalyst.

The supported metallocene catalyst I or II obtained as described above may be further combined with an organic aluminum compound (component (D')) to obtain an olefin polymerization catalyst that may be suitably for production of an olefin polymer of the invention.

The component (D') used in combination with the supported metallocene catalyst I or II for production of an olefin polymer may be selected from among the aforementioned organic aluminum compounds used for production of the supported metallocene catalyst I or II, and it may be the same organic aluminum compound used for production of the supported metallocene catalyst I or II, or a different organic aluminum compound:

The amount of component (D') used for production of the olefin polymer is in a proportion of 1–5000 moles, preferably 5–3000 moles and more preferably 10–1000 moles in terms of Al atoms in component (D') with respect to 1 mole of the transition metal atom of the metallocene compound (a) in the supported metallocene catalyst or preactivated supported metallocene catalyst.

The amount of the supported metallocene catalyst or preactivated supported metallocene catalyst used per liter of polymerization volume is $1\times10^{-10}$ to $1\times10^{-3}$ mol and preferably $1\times10^{-9}$ to $1\times10^{-4}$ mol in terms of transition metal atoms of the metallocene compound (a) in the catalyst. An amount of catalyst within this range will allow an efficient and controlled olefin polymerization reaction rate to be maintained.

The term "polymerization volume" means the volume of the liquid-phase portion in the polymerization vessel in the case of liquid-phase polymerization, or the volume of the gas-phase portion in the polymerization vessel in the case of gas-phase polymerization.

The olefin polymer production process of the invention is an olefin polymer production process which employs an olefin polymerization catalyst according to any one of (1) to (3) above, which contains a metallocene compound according to the invention In the olefin polymer production process of the invention, the metallocene compound is preferably used in its racemic form to produce olefin polymers exhibiting the desired performance. A small amount (preferably less than 5%) of the meso form may be included with the racemic form, to a degree which will not impair the intended quality.

The process in which the olefin polymer production process of the invention is applied may be a publicly known olefin polymerization process, and for example, a slurry polymerization process may be employed wherein the olefin is polymerized in an inert solvent, specifically an aliphatic hydrocarbon such as butane, pentane, hexane, heptane or isooctane, an alicyclic hydrocarbon such as cyclopentane, cyclohexane or methylcyclohexane, an aromatic hydrocarbon such as toluene, xylene or ethylbenzene or a gasoline fraction or hydrogenated diesel fraction. Alternatively, there may be employed bulk polymerization using the olefin itself as the solvent, or gas-phase polymerization wherein the olefin is polymerized in a gas phase. Two or more different processes may also be combined as the polymerization process. A preferred combination of polymerization processes is a combination wherein the first stage is carried out by bulk polymerization and the subsequent second stage is carried out by gas-phase polymerization. A solution polymerization process may also be employed.

The olefin polymer production process of the invention may use a polymerization temperature of −50° C. to 150° C., preferably 20° C. to 120° C. and more preferably 40° C. to 100° C., and a polymerization pressure of from atmospheric pressure to 9.9 MPa (gauge pressure) and preferably 0.4–5.0 MPa (gauge pressure). If necessary, a chain transfer agent such as hydrogen may be introduced to adjust the molecular weight of the obtained olefin polymer.

After completion of the polymerization reaction, the unreacted monomer and hydrogen are separated from the polymerization system and subjected to catalyst-inactivation treatment and the like to obtain the olefin polymer.

The olefin polymer of the invention is produced by the olefin polymer production process explained above.

An "olefin" according to the invention refers to an olefin of 2–20 carbons, and specifically ethylene, propylene, 1-butene, 1-pentene, 1-hexene, 1-heptene, 1-octene, 1-decene, 1-dodecene, 1-hexadecene, 4-methyl-1-pentene, styrene, vinylcyclohexane, dienes, trienes and the like. An "olefin other than propylene" according to the invention refers to an olefin of 2–20 carbons, and specifically ethylene, 1-butene, 1-pentene, 1-hexene, 1-heptene, 1-octene, 1-decene, 1-dodecene, 1-hexadecene, 4-methyl-1-pentene, and the like, as well as mixtures of two or more thereof. According to the invention, the most preferred olefins other than propylene are ethylene and/or 1-butene.

An "olefin polymer" according to the invention refers to a homopolymer comprising one olefin selected from among olefins of 2–20 carbons, or a copolymer comprising two or more olefins.

The "olefin polymer", "propylene homopolymer" and "propylene/olefin copolymer" according to the invention may also include as structural units thereof styrene, vinylcyclohexane, dienes, trienes and the like in a range of no greater than 30 mole percent based on the moles of the polymer or copolymer.

The olefin polymer of the invention is preferably a propylene/olefin copolymer comprising a propylene unit and an olefin unit other than propylene as structural units, with an olefin unit content in the copolymer of 0.1–80 mole percent based on the moles of copolymer. The olefin unit content in the copolymer is preferably 0.5–50 mole percent, more preferably 1–30 mole percent and even more preferably 1–15 mole percent.

When the olefin polymer obtained by the production process of the invention is a propylene/olefin copolymer comprising a propylene unit and an olefin unit other than propylene as structural units, it may be a random copolymer, block copolymer or random block copolymer.

When the olefin polymer of the invention is a block copolymer, it is preferably obtained by using an olefin polymerization catalyst comprising a metallocene compound of the invention to produce in the first step a propylene homopolymer (I) (hereinafter also referred to as "segment A"), and then to produce in the second step a propylene/olefin random copolymer (II) (hereinafter also referred to as "segment B") comprising a propylene unit and an olefin unit other than propylene as structural units and having a propylene unit content of 10–90 mole percent and preferably 20–80 mole percent based on the moles of copolymer (II). Preferably, the content of segment A is 10–95 wt % and the content of segment B is 90–5 wt % based on the weight of the block copolymer. The resulting polymer may be referred to as a propylene//propylene/olefin block copolymer.

When the olefin polymer of the invention is a random block copolymer, it is preferably obtained by using an olefin polymerization catalyst comprising a metallocene compound of the invention to produce in the first step a propylene/olefin random copolymer (I) (hereinafter also referred to as "segment A") comprising a propylene unit and an olefin unit other than propylene as structural units, wherein the content of the olefin unit other than propylene is 0.1–30 mole percent, preferably 0.3–20 mole percent and more preferably 0.5–10 mole percent based on the moles of copolymer (I), and then to produce in the second step a propylene/olefin random copolymer (II) (hereinafter also referred to as "segment B") comprising a propylene unit and an olefin unit other than propylene as structural units, wherein the content of the propylene unit is 10–90 mole percent and preferably 20–80 mole percent based on the moles of copolymer (II). Preferably; the content of segment A is 10–95 wt % and the content of segment B is 90–5 wt % based on the weight of the random block copolymer. The resulting polymer may be referred to as a propylene/olefin//propylene/olefin random block copolymer.

In the above-mentioned propylene//propylene/olefin block copolymer and propylene/olefin//propylene/olefin random block copolymer, the melt flow rate (MFR) of the propylene/olefin random copolymer as segment B is preferably no greater than 300 g/10 min, more preferably no greater than 100 g/10 min, even more preferably no greater than 10 g/10 min and still preferably no greater than 1 g/10 min to obtain molded articles with the good impact resistance, transparency or flexibility. It is especially preferred to be no greater than 0.1 g/10 min, and is most preferably no greater than 0.01 g/10 min. The "melt flow rate (MFR)" as used for the invention is the value (units: g/10 min) measured according to JIS K7210 with a load of 21.18 N at a temperature of 230° C.

In the above-mentioned propylene//propylene/olefin block copolymer and propylene/olefin//propylene/olefin random block copolymer, the MFR of segment B (hereinafter also referred to as "$MFR_B$") may be calculated by the following formula, using the MFR of the copolymer (hereinafter also referred to as "$MFR_T$"), the content of segment A in the copolymer (hereinafter also referred to as "$W_A$", units: wt %), the MFR of segment A in the copolymer (hereinafter also referred to as "$MFR_A$") and the content of segment B in the copolymer (hereinafter referred to as "$W_B$", units: wt %).

$$\log(MFR_B) = (100/W_B) \times \{\log(MFR_T) - (W_A/100) \times \log(MFR_A)\}$$

According to the invention, the block copolymerization or random block copolymerization is carried out using an olefin polymerization catalyst comprising a metallocene compound of the invention, first under conditions with a temperature of 30–100° C and preferably 50–80° C. and a pressure of 0.3–5 MPa and preferably 1–4 MPa for a period of 0.5–10 hours and preferably 1–5 hours, in the first step. The second subsequent steps are then carried out at a temperature of 30–100° C. and preferably 50–80° C. and a pressure of 0.3–5 MPa and preferably 1–4 MPa for a period of 0.5–10 hours and preferably 1–5 hours. By using hydrogen as a chain transfer agent in both the first and second steps it is possible to adjust the MFR of the polymer obtained in each step to the desired range. The first and second steps may each include a plurality of steps, but preferably they both consist of a single step.

When the olefin polymer of the invention is a block copolymer or random block copolymer, the soluble fraction of the olefin polymer in o-dichlorobenzene at 0° C. is preferably no greater than 30 wt %, more preferably no greater than 15 wt %, even more preferably no greater than 10 wt %, especially no greater than 5 wt % and most preferably no greater than 0.5 wt %.

The soluble fraction in o-dichlorobenzene at 0° C. is determined by the following fractionation method. Specifically, first a fractionation column prepared by packing 0.1 mm-diameter glass beads into a stainless steel tube with a length of 15 cm and an inner diameter of 0.46 cm (packing the full 15 cm of the tube) is kept at 140° C. and 0.5 ml of a sample of the polymer dissolved in o-dichlorobenzene at a temperature of about 140° C. to a polymer concentration of 2 mg/ml is supplied and retained therein. Next, the temperature of the fractionation column is lowered to 0° C. at a rate of 1° C./min, to allow the polymer in the sample to precipitate on the surfaces of the glass beads. The temperature of the fractionation column is then kept at 0° C. while o-dichlorobenzene at 0° C. is passed through the fractionation column for 2 minutes at a flow rate of 1 ml/min to dissolve the soluble polymer component in the o-dichlorobenzene at 0° C. and obtain an extract. Next, the molecular weight distribution of the polymer in the extract is measured with an infrared detector (wavelength: 3.42 μm). This procedure is then repeated, gradually increasing the temperature of the fractionation column and the o-dichlorobenzene (extract temperature) 10° C. at a time in the range of 0–50° C., 5° C. at a time in the range of 50–90° C. and 3° C. in the range of 90–140° C., and the polymer component eluting into the o-dichlorobenzene at each temperature and the polymer weight percentage and molecular weight of each fraction are calculated to draw an extraction temperature (° C.) vs. weight percentage (wt %) elution curve from which the elution of each component is calculated. The aforementioned fractionation method is described in detail by Takao Usami et al. in Journal of Applied Polymer Science: Applied Polymer Symposium, 52, 145–158(1993). The soluble fraction of the olefin polymer in o-dichlorobenzene at 0° C. may be determined as the soluble component fraction at 0° C. via this fractionation method.

When the olefin polymer of the invention is a copolymer comprising a propylene unit and an olefin unit other than propylene as structural units, and particularly when it is a propylene/olefin random copolymer, the relationship between the propylene unit content of the copolymer (P: mole percent) and the melting point of the copolymer (Tm: ° C.) preferably satisfies the following inequality:

$$170 > Tm \geq 145 - 5.5(100 - P)$$

The relationship more preferably satisfies the following inequality:

$$170 > Tm \geq 147 - 5.5(100 - P)$$

These inequalities indicate the particularly excellent property of an olefin polymer of the invention whereby a high melting point can be exhibited even when the olefin unit content of the copolymer is high.

The olefin polymer of the invention has a weight-average molecular weight (Mw) of preferably $5 \times 10^4 - 5 \times 10^5$ g/mol and more preferably $1 \times 10^5 - 5 \times 10^5$ g/mol. The ratio (Mw/Mn) of the weight-average molecular weight (Mw) and the number-average molecular weight (Mn) is preferably 1.5–3.8, more preferably 1.5–3.5, even more preferably 1.8–3.0, and most preferably 1.8–2.5.

The olefin polymer of the invention has an MFR of preferably 0.5–300 g/10 min and more preferably 0.5–100 g/10 min. If the MFR is smaller than 0.5 g/10 min or greater than 300 g/10 min, it may be difficult to accomplish molding with conventional publicly known molding machines.

The isotactic pentad fraction ($I_5$) representing the stereoregularity of the olefin polymer of the invention is not particularly restricted but is preferably 0.400–0.990, more preferably 0.800–0.990, even more preferably 0.850–0.990, and most preferably 0.920–0.990.

The isotactic triad fraction ($I_3$) of the olefin polymer of the invention is not particularly restricted but is preferably 0.50–0.999, more preferably 0.85–0.999, even more preferably 0.87–0.999, and most preferably 0.94–0.999.

There are no particular restrictions on the proportion of the number of moles of the olefin unit derived from 2,1-insertion reaction of the olefin and the number of moles of the propylene unit derived from 1,3-insertion reaction of the olefin, with respect to the total moles of the olefin unit composing the olefin polymer of the invention, but these should be each independently no greater than 5 mol % and preferably smaller than 3 mol %.

The isotactic pentad fraction ($I_5$) and the isotactic triad fraction ($I_3$) of the olefin polymer of the invention, as well as the proportion of the number of moles of the olefin unit derived from 2,1-insertion reaction of the olefin and the number of moles of the olefin unit derived from 1,3-insertion reaction of the olefin, with respect to the total moles of the olefin unit composing the olefin polymer, may be determined based on the results of measuring the $^{13}C$ nuclear magnetic resonance spectrum, according to the following method.

Specifically, the sample (olefin polymer) is dissolved in a solution mixture of o-dichlorobenzene/benzene bromide=8/2 (weight ratio) to a concentration of 20 wt % in the solution mixture. The $^{13}C$ nuclear magnetic resonance spectrum of the sample solution is measured at a wavelength of 67.20 MHz and a temperature of 130° C. The measuring apparatus used may be, for example, "JEOL-GX270NMR" by JEOL Co., Ltd.

For an olefin homopolymer, the "isotactic pentad fraction ($I_5$)" and "isotactic triad fraction ($I_3$)" are indicators of the stereoregularity of the polymer, determined by $^{13}C$ NMR spectroscopy as proposed by A. Zambelli et al. in Macromolecules, 6, 925–926(1973). The peaks in the $^{13}C$ NMR spectroscopy were assigned according to the method proposed by A. Zambelli et al. in Macromolecules, 8, 687 (1975). The isotactic triad fraction ($I_3$) of the copolymer was calculated according to the method proposed in Japanese Patent Kokai H7-149833 and Japanese Patent Kokai H8-283343.

The isotactic pentad fraction ($I_5$) is the proportion of five continuous meso bond-forming olefin units with respect to the total number of olefin units composing the olefin polymer, and the isotactic triad fraction ($I_3$) is the proportion of three continuous meso bond-forming olefin units with respect to the total number of olefin units in the molecular chain of the olefin polymer. A higher isotactic pentad fraction ($I_5$) and isotactic triad fraction ($I_3$) therefore indicate higher isotacticity. In particular, the isotactic pentad fraction ($I_5$) is used as an index of the isotacticity of a homopolymer, while the isotactic triad fraction ($I_3$) is used as an index of the isotacticity of a homopolymer or copolymer.

The proportion of the number of moles of olefin units derived from 2,1-insertion reaction of the olefin and of the number of moles of olefin units derived from 1,3-insertion reaction of the olefin, with respect to the total moles of olefin units composing the olefin polymer, is each an index of the stereoregularity of the olefin polymer, and is determined by $^{13}C$ NMR spectroscopy based on the method published by T. Tsutui et al. in Polymer, 30, 1350–1356(1989).

The olefin polymer of the invention is usually subjected to hot-melt kneading at a temperature of 190–350° C. for about 20 seconds to 30 minutes using a melt kneading apparatus, if necessary after addition of various additives such as antioxidants, ultraviolet absorbers, antistatic agents, nucleating agents, lubricants, flame retardants, anti-blocking agents, coloring agents, inorganic or organic fillers and the like, and any of various synthetic resins, and is extruded into a strand form if necessary and then chopped in a granular form, i.e. pellets, for supply to a process for production of various molded articles. For example, it may be suitably used to prepare films, sheets, fibers, injection molded articles, blow-molded articles, containers, drawn yarn, non-woven fabrics, foam articles and the like, or it may be appropriately used as a sealant.

EXAMPLES

The present invention will now be explained in further detail by way of examples and comparative examples, which are not intended to be limitative on the invention. The definitions of terms and the measurement examples used in the examples and comparative examples are as follows.

(1) Melt flow rate (MFR) (units: g/10 min): Measured according to JIS K7210 under Condition 14 in Table 1 (21.18 N load, 230° C. temperature).

(2) Weight-average molecular weight (Mw) and its ratio to number-average molecular weight (Mn) (Mw/Mn): Determined by gel permeation chromatography (GPC), using a "PSKgel GMH6-HT" by Toso Co., Ltd. as the column and a "GPC-150C" by Walters Co. as the measuring apparatus; the sample (olefin polymer) was dissolved in o-dichlorobenzene to a concentration of 0.05 wt % and the resulting solution was measured at a temperature of 135° C.

(3) Melting point (units: ° C.): Measured using a "DSC7 differential scanning calorimeter" by Perkin Elmer. The melting point Tm of the olefin polymer by the measuring apparatus is a value determined as a temperature showing a peak on melting which was determined by heating the polymer from room temperature to 230° C. at rate of 30° C./min, keeping it at 230° C. for 10 minutes, followed by lowing to –20° C. at a rate of 20° C./min, keeping it at –20° C. for further 10 minutes and heating it again at a rate of 20° C./min.

(4) Olefin unit content where olefin polymer is a propylene/olefin copolymer comprising a propylene unit and an olefin unit other than propylene as the structural units (units: mol %): Determined by $^{13}C$ NMR spectroscopy.

(5) Soluble fraction of olefin polymer at 0° C., continuously or gradually raising the temperature of the o-dichlorobenzene and measuring the dissolution of the olefin polymer at each temperature (units: wt %): Calculated by the fractionation method described above, using o-dichlorobenzene.

(6) Haze (units: %): Measured according to the method described in JIS K7105, using a sample with a thickness of 0.4 mm.

(7) Isotactic pentad fraction ($I_5$): Measured by the method described above, using a "JEOL-GX270" by JEOL Co., Ltd. as the measuring apparatus.

(8) Proportion of the number of moles of the olefin unit derived from 2,1-insertion reaction of the olefin and the number of moles of the propylene unit derived from 1,3-insertion reaction of the olefin, with respect to the total moles of the olefin unit composing the olefin polymer (units: mol %): Measured by the method described above, using a "JEOL-GX270" by JEOL Co., Ltd. as the measuring apparatus. The minimum detection limit was 0.02 mol %.

(9) Content of segment A and segment B where the olefin polymer is a block copolymer or random block copolymer (units: wt %): Following the aforementioned method for measuring the dissolution of the olefin polymer in o-dichlorobenzene, first the dissolution of the olefin polymer of segment A alone is measured at each temperature as the temperature of the o-dichlorobenzene is continuously or gradually increased, and then the dissolution of the olefin polymer comprising segment A and segment B is measured at each temperature as the temperature of the o-dichlorobenzene is continuously or gradually increased, and the portion corresponding to segment A is subtracted to calculate the wt % of the portion corresponding to segment B.

Example 1

Synthesis of rac-dimethylsilylenebis(2-(2-(5-methyl)-furyl)-4-phenyl-indenyl)zirconium dichloride (1) Synthesis of dimethylbis(2-(2-(5-methyl)-furyl)-4-phenyl-indenyl)silane After adding 12 g (0.045 mol) of 2-(2-(5-methyl)-furyl)-4-phenyl-indene, 0.3 g (2.5 mmol) of copper isocyanate and 150 ml of tetrahydrofuran to a 200 ml glass reactor, the mixture was cooled to –70° C. in a dry ice/methanol bath. Next, 30 ml (0.045 mol) of a 1.50 mol/L n-butyllithium/hexane solution was added dropwise thereto. After the dropwise addition, the mixture was stirred for 16 hours while gradually returning it to room temperature. It was again cooled to –50° C. in a dry ice/methanol bath, and 40 ml of a tetrahydrofuran solution containing 2.9 g (0.022 mol) of dimethyldichlorosilane was added dropwise. After the dropwise addition, the mixture was stirred for 16 hours while gradually returning it to room temperature.

Distilled water was added to the reaction solution which was then transferred to a separatory funnel and washed with saline solution to neutrality. Anhydrous sodium sulfate was added thereto, and the mixture was allowed to stand overnight to dry the reaction solution. The anhydrous sodium sulfate was filtered out, the solvent was distilled off under reduced pressure, and purification was performed with a silica gel column to obtain 11 g of dimethylbis(2-(2-(5-methyl)-furyl)-4-phenyl-indenyl)silane as a light yellow liquid (82% yield)

(2) Synthesis of rac-dimethylsilylenebis(2-(2-(5-methyl)-furyl)-4-phenyl-indenyl)zirconium dichloride After adding 5.3 g (8.8 mmol) of dimethylbis(2-(2-(5-methyl)-furyl)-4-phenyl-indenyl)silane and 150 ml of diethyl ether to a 100 ml glass reactor, the mixture was cooled to −70° C. in a dry ice/methanol bath. Next, 12 ml (18 mmol) of a 1.50 mol/L n-butyllithium/hexane solution was added dropwise thereto. After the dropwise addition, the mixture was stirred for 16 hours while returning it to room temperature. The solvent of the reaction solution was concentrated under reduced pressure to about 20 ml, 200 ml of toluene was added, and the mixture was cooled to −70° C. in a dry ice/methanol bath. To this there was added 2.0 g (8.6 mmol) of zirconium tetrachloride. The mixture was then stirred for 3 days while gradually returning it to room temperature. As a result of NMR measurement of a portion of the reaction solution, no peak attributable to the meso form was confirmed.

The solvent was distilled off under reduced pressure, recrystallization was performed with dichloromethane/hexane to obtain 3.0 g of a dimethylsilylenebis(2-(2-(5-methyl)-furyl)-4-phenyl-indenyl)zirconium dichloride racemate (≧99% purity) as yellow-orange crystals (45% yield). The proton NMR ($^1$H-NMR) data for the obtained racemate are as follows. <Identification by $^1$H-NMR(CDCl$_3$)>

Racemic: δ 1.15 (s, 6H), δ 2.42 (s, 6H), δ 6.06 (d, 2H), δ 6.26 (d, 2H), δ 6.81 (dd, 2H) , δ 6.93 (d, 2H), δ 7.03 (s, 2H), δ 7.31–δ 7.64 (m, 12H).

Production of propylene homopolymer using rac-dimethylsilylenebis(2-(2-(5-methyl)-furyl)-4-phenyl-indenyl)zirconium dichloride as catalyst component In an SUS autoclave there were loaded in order 1 L of toluene, a methylaluminoxane/toluene solution ("MMAO3A", product of Tosoh Akzo) (Al/Zr=10,000) and 3 ml (0.29×10$^{-6}$ mol) of a rac-dimethylsilylenebis(2-(2-(5-methyl)-furyl)-4-phenyl-indenyl)zirconium dichloride/toluene solution, and the mixture was heated to 30° C. Propylene was introduced under a pressure of 0.3 MPa for one hour of polymerization. After the polymerization, the polymer was filtered off and the catalyst component was decomposed with 1 liter of acidic methanol. This was followed by filtration, washing and drying in that order, to obtain 32 g of propylene homopolymer. The polymerization activity was 110 kg-polymer/mmol(Zr)·hr. Upon analysis of the obtained propylene homopolymer, the MFR was 0.03 g/10 min, the isotactic pentad factor (I$_5$) was 0.973, the proportion of the number of moles of the propylene unit derived from 2,1-insertion reaction of the propylene monomer with respect to the total number of moles of the propylene unit of the propylene homopolymer was 0.22 mol %, the number of moles of the propylene unit derived from 1,3-insertion reaction of the propylene monomer with respect to the total number of moles of the propylene unit of the propylene homopolymer was 0.05 mol %, the Mw was 7.33×10$^5$ g/mol, the Mw/Mn ratio was 2.22 and the melting point was 159.1° C.

Example 2

Production of Preactivated Supported Metallocene Catalyst (1) Production of Supported Metallocene Catalyst After loading 89 ml (267 mmol in terms of Al atoms) of a toluene solution containing methylaluminoxane (concentration: 3 mol/liter; "PMAO", product of Tosoh Akzo Co., Ltd.) and 0.929 millimoles of the dimethylsilylenebis(2-(2-(5-methyl)-furyl)-4-phenyl-indenyl) zirconium dichloride racemate synthesized in Example 1 as a metallocene compound into a nitrogen gas-substituted stirrer-equipped glass reactor with an inner volume of 500 ml, the mixture was stirred and kept at 25° C. for 15 minutes for reaction to obtain the reaction product of the metallocene compound and aluminoxane, i.e. a metallocene catalyst. Next, 6.7 g of silica with a mean particle size of 51 μm ("SYLOPOL(R) 948", product of Grace Davison Co.) which had been calcined for 8 hours at a temperature of 750° C. under reduced pressure was loaded into the reactor, the temperature of the reactor was raised to 110° C. and kept at that temperature for 60 minutes while stirring for contact reaction between the silica and the above-mentioned reaction product, to obtain a slurry containing a crude supported metallocene catalyst carrying the metallocene catalyst.

After then cooling the reactor to −10° C., the reactor temperature was kept at −10° C. while loading 250 ml of n-hexane and stirring for 10 minutes, and then the stirring was suspended and the solvent was separated by decantation. The reactor temperature was kept at −10° C. while loading 250 ml of n-hexane into the reactor and performing stirred washing for 5 minutes, and then the stirring was suspended and the washing solvent was separated by decantation. The washing procedure was repeated 4 times to obtain a purified supported metallocene catalyst. Finally, 250 ml of n-hexane was loaded into the reactor and the supported metallocene catalyst was dispersed to prepare a slurry.

(2) Production of Preactivated Supported Metallocene Catalyst

The slurry of the supported metallocene catalyst and n-hexane obtained in (1) above was transferred into a nitrogen gas-substituted stirrer-equipped glass reactor with an inner volume of 500 ml, and the reactor temperature was adjusted to 0° C. The reactor temperature was then stirred and kept at 0° C. while supplying a propylene/hydrogen mixed gas in a molar ratio of 10:1 at a supply rate of 300 ml/min for a period of 40 minutes to accomplish prepolymerization, in order to obtain a reaction mixture containing a crude preactivated supported metallocene catalyst having an olefin polymer carried on a supported metallocene catalyst.

After separating the n-hexane solvent from the reaction mixture by decantation, 250 ml of n-hexane was loaded and the mixture was stirred for 5 minutes to wash the preactivated supported metallocene catalyst, and the washing solvent was separated by decantation. The washing procedure was repeated 5 times. Next, 250 ml of n-hexane was loaded into the reactor and the preactivated supported metallocene catalyst was dispersed in the n-hexane to prepare a slurry. After filtering out the solvent of the slurry containing the preactivated supported metallocene catalyst and n-hexane, drying was performed under reduced pressure at a temperature of 25° C. to obtain a preactivated supported metallocene catalyst composed of solid particles. This preactivated supported metallocene catalyst was analyzed to determine the number of grams of propylene polymer carried per gram of supported metallocene catalyst. The results indicated that 1 gram of propylene polymer was carried per gram of the supported catalyst prior to preactivation.

Production of Propylene/ethylene Copolymer

The interior of a thoroughly nitrogen-substituted horizontal gas-phase reactor with an inner volume of 3 liters was heated to 75° C., 150 g of propylene polymer crude particles and 0.5 millimole of triethylaluminum were added and the mixture was stirred at 85 rpm for 5 minutes. The preactivated supported metallocene catalyst prepared in the manner described above was then added in an amount of 22 mg in terms of the supported metallocene catalyst prior to preactivation, and the mixture was stirred for 5 minutes. A propylene/ethylene mixed monomer was then supplied to the reactor, the reaction pressure was increased to 2.3 MPa (gauge pressure) while maintaining an ethylene monomer concentration of 8 mol % in the reactor, and polymerization was carried out under constant polymerization conditions of 75° C. and 2.6 MPa (gauge pressure). When the resulting propylene/ethylene copolymer amount reached 300 g the monomer supply was interrupted, the pressure was lowered to atmospheric pressure, and 300 g of powdered polymer was drawn out from the reactor under a nitrogen stream.

The same polymerization was then carried out twice in the same manner as above but using 150 g of the powdered polymer remaining in the reactor after the drawing out procedure instead of the 150 g of propylene polymer crude particles, and the result of the third polymerization was used for calculation of the polymerization activity and analysis of the obtained propylene/ethylene copolymer. The polymerization time was approximately 1.5 hours for each procedure.

The polymerization activity was 10,200 g ·polymer/g ·catalyst, in terms of one gram of the supported catalyst prior to preactivation. Upon analysis of the propylene/ethylene copolymer, the ratio of the weight-average molecular weight (Mw) to the number-average molecular weight (Mn) (Mw/Mn) was 2.5, the MFR was 7.1 g/10 min, the ethylene unit content was 4.87 mol % and the melting point was 125° C. The obtained propylene/ethylene copolymer therefore satisfied the relational inequality 170>Tm≧145–5.5(100–P)

Example 3

Production of propylene homopolymer using rac-dimethylsilylenebis (2-(2-(5-methyl)-furyl)-4-phenyl-indenyl) zirconium dichloride as catalyst component After adding a methylaluminoxane/toluene solution ("MMAO3A", product of Tosoh Akzo) to an SUS autoclave at $4.5 \times 10^{-3}$ mol in terms of Al, 1 L of liquefied propylene was added and the temperature was raised to 50° C. Separately, the dimethylsilylenebis(2-(2-(5-methyl)-furyl)-4-phenyl-indenyl) zirconium dichloride racemate synthesized in Example 1 ($0.20 \times 10^{-6}$ mol) and a methylaluminoxane/toluene solution ("MMAO3A", product of Tosoh Akzo) ($3.0 \times 10^{-3}$ mol in terms of Al) were reacted for 15 minutes, after which the reaction solution was injected into an autoclave to initiate polymerization reaction for propylene homopolymerization at 50° C. for 20 minutes. The polymerization reaction was suspended by addition of a small amount of methanol, and then the product was delimed with a strong alkali solution and dried to obtain 23.2 g of a propylene homopolymer. The polymerization activity was 346 kg-polymer/mmol(Zr)·hr. Upon analysis of the obtained propylene homopolymer, the MFR was 0.014 g/10 min, the Mw/Mn ratio was 2.8 and the melting point was 160.3° C.

Example 4

Production of propylene/ethylene copolymer with preactivated supported metallocene catalyst using rac-dimethylsilylenebis (2-(2-(5-methyl)-furyl)-4-phenyl-indenyl) zirconium dichloride After loading 0.5 mmol of triethylaluminum, 4.1 mmol of hydrogen and 1 L of liquefied propylene into a thoroughly nitrogen-substituted reactor with an inner volume of 1.5 liters, the temperature was raised to 60° C. and stabilized. The pressure in the reactor was 2.50 MPa (gauge pressure). After feeding in ethylene so that the pressure in the reactor was 0.25 MPa higher than the pressure before loading, i.e. 2.75 MPa (gauge pressure) and stabilizing the pressure, the temperature inside the reactor was raised to 70° C. and the temperature and pressure in the reactor were further stabilized. Next, 18 mg of the preactivated supported metallocene catalyst prepared in Example 2 suspended in 10 ml of n-hexane was supplied to the reactor to initiate polymerization reaction for copolymerization of propylene and ethylene at 70° C. over a period of 30 minutes. As a result, 105 g of propylene/ethylene copolymer was obtained, and the polymerization activity was 23,333 g·polymer/g·catalyst·hr, in terms of one gram of the supported catalyst prior to preactivation. Upon analysis of the propylene/ethylene copolymer, the MFR was 5.0 g/10 min, the ethylene unit content was 3.7 mol %, the melting point was 127° C. and the haze was 15%. The obtained propylene/ethylene copolymer therefore satisfied the relational inequality 170 >Tm ≧145–5.5(100-P).

Example 5

Production of propylene//ethylene/propylene block copolymer

After nitrogen substitution of a stainless steel stirrer-equipped polymerization vessel with an interior volume of 1.5 L, 0.5 mmol of triethylaluminum (1 mol/L concentration n-hexane solution), 100 ml of hydrogen and 800 ml of liquefied propylene were loaded. After then raising the temperature of the polymerization vessel to 60° C., the preactivated catalyst obtained in Example 2 slurrified in 5 ml of n-hexane was injected into the polymerization vessel at 10.7 mg in terms of the supported catalyst prior to preactivation, together with 200 ml of liquefied propylene, and polymerization was initiated. After initiating polymerization, the temperature in the polymerization vessel was raised to and kept at 70° C., and the polymerization reaction was continued for one hour. After elapse of the polymerization time, the unreacted polymer was eliminated out of the system while lowering the temperature of the polymerization vessel to 25° C., and then a portion (32.8 g) of the reaction product was drawn out and used as a sample of the propylene polymer corresponding to segment A (propylene homopolymer block component).

Next, 0.5 mmol of triethylaluminum (1 mol/L concentration n-hexane solution) was added with the reaction product remaining in the polymerization vessel, the temperature in the polymerization vessel was raised to and kept at 50° C., an ethylene/propylene mixed gas (molar ratio: ethylene/propylene =85/15) was supplied to maintain an internal pressure of 1.5 MPa in the polymerization vessel, and gas-phase copolymerization of ethylene/propylene was continued for 200 minutes. After elapse of the polymerization time, supply of the ethylene/propylene mixed gas was interrupted and the unreacted mixed gas was eliminated out of the system while lowering the temperature of the polymerization vessel to 25° C., to obtain 165.8 g of a particulate reaction product (propylene//ethylene/propylene block copolymer). The polymerization vessel was opened and observed after completion of the polymerization, but no lump polymer and no polymer adhesion on polymerization vessel wall was found.

The obtained propylene//ethylene/propylene block copolymer had an ethylene unit content of 35.2 mol %, a BD of 440 kg/m$^3$, an intrinsic viscosity ([η]w) of 1.62 dl/g, a Tm of 154.2° C. and an MFR of 2.57 g/10 min, while the soluble fraction at 0° C., where the dissolution of the olefin polymer was measured at various temperatures while continuously or gradually raising the temperature of the o-dichlorobenzene, was 7.0 wt % and the haze was 54.7%. The obtained propylene//ethylene/propylene block copolymer also contained 62.4 wt % of segment A (propylene homopolymer block component) and 37.6 wt % of segment B (ethylene/propylene copolymer block component). By calculation, the ethylene unit content of segment B was 78.4 mol % and the MFR was 0.74 g/10 min. The polymerization activity of the catalyst was calculated to be 3600 g·polymer/g·catalyst·hr in terms of one gram of the supported catalyst before preactivation.

Example 6

Production of propylene//ethylene/propylene block copolymer

After nitrogen substitution of a stainless steel stirrer-equipped polymerization vessel with an interior volume of 1.5 L, 0.5 mmol of triethylaluminum (1 mol/L concentration n-hexane solution), 100 ml of hydrogen and 800 ml of liquefied propylene were loaded. After then raising the temperature of the polymerization vessel to 60° C., the preactivated catalyst obtained in Example 2 slurrified in 5 ml of n-hexane was injected into the polymerization vessel at 12.3 mg in terms of the supported catalyst prior to preactivation, together with 200 ml of liquefied propylene, and polymerization was initiated. After initiating polymerization, the temperature in the polymerization vessel was raised to and kept at 70° C., and the polymerization reaction was continued for one hour. After elapse of the polymerization time, the unreacted polymer was eliminated out of the system while lowering the temperature of the polymerization vessel to 25° C., and then a portion (33.0 g) of the reaction product was drawn out and used as a sample of the propylene polymer corresponding to segment A (propylene homopolymer block component).

Next, the temperature in the polymerization vessel was raised to and kept at 50° C. with the reaction product remaining in the polymerization vessel, an ethylene/propylene mixed gas (molar ratio: ethylene/propylene=92/8) was supplied to maintain an internal pressure of 1.5 MPa in the polymerization vessel, and gas-phase copolymerization of ethylene/propylene was continued for 240 minutes. After elapse of the polymerization time, supply of the ethylene/propylene mixed gas was interrupted, and the unreacted mixed gas was eliminated out of the system while lowering the temperature of the polymerization vessel to 25° C., to obtain 232.3 g of a particulate reaction product (propylene//ethylene/propylene block copolymer). The polymerization vessel was opened and observed after completion of the polymerization, but no lump polymer and no polymer adhesion on polymerization vessel wall was found.

The obtained propylene//ethylene/propylene block copolymer had an ethylene unit content of 35.0 mol %, a BD of 450 kg/m$^3$, an intrinsic viscosity ([η]w) of 2.22 dl/g, a Tm of 154.8° C. and an MFR of 0.72 g/10 min, while the soluble fraction at 0° C., where the dissolution of the olefin polymer was measured at various temperatures while continuously or gradually raising the temperature of the o-dichlorobenzene, was 0 (zero) wt % and the haze was 13.6%. The obtained propylene//ethylene/propylene block copolymer also contained 59.3 wt % of segment A (propylene homopolymer block component) and 40.7 wt % of segment B (ethylene/propylene copolymer block component). By calculation, the ethylene unit content of segment B was 73.5 mol % and the MFR was 0.03 g/10 min. The polymerization activity of the catalyst was calculated to be 3800 g·polymer/g·catalyst·hr in terms of one gram of the supported catalyst before preactivation.

Example 7

Production of propylene//ethylene/propylene block copolymer

After nitrogen substitution of a stainless steel stirrer-equipped polymerization vessel with an interior volume of 1.5 L, 0.5 mmol of triethylaluminum (1 mol/L concentration n-hexane solution), 100 ml of hydrogen and 800 ml of liquefied propylene were loaded. After then raising the temperature of the polymerization vessel to 60° C., the preactivated catalyst obtained in Example 2 slurrified in 5 ml of n-hexane was injected into the polymerization vessel at 12.2 mg in terms of the supported catalyst prior to preactivation, together with 200 ml of liquefied propylene, and polymerization was initiated. After initiating polymerization, the temperature in the polymerization vessel was raised to and kept at 70° C., and the polymerization reaction was continued for one hour. After elapse of the polymerization time, the unreacted polymer was eliminated out of the system while lowering the temperature of the polymerization vessel to 25° C., and then a portion (37.3 g) of the reaction product was drawn out and used as a sample of the propylene polymer corresponding to segment A (propylene homopolymer block component).

Next, the temperature in the polymerization vessel was raised to and kept at 50° C. with the reaction product remaining in the polymerization vessel, an ethylene/propylene mixed gas (molar ratio: ethylene/propylene=77/23) was supplied to maintain an internal pressure of 1.5 MPa in the polymerization vessel, and gas-phase copolymerization of ethylene/propylene was continued for 220 minutes. After elapse of the polymerization time, supply of the ethylene/propylene mixed gas was interrupted, and the unreacted mixed gas was eliminated out of the system while lowering the temperature of the polymerization vessel to 25° C., to obtain 197.6 g of a particulate reaction product (propylene//ethylene/propylene block copolymer). The polymerization vessel was opened and observed after completion of the polymerization, but no lump polymer and no polymer adhesion on polymerization vessel wall was found.

The obtained propylene//ethylene/propylene block copolymer had an ethylene unit content of 21.1 mol %, a BD of 440 kg/m$^3$, an intrinsic viscosity ([η]w) of 1.57 dl/g, a Tm of 154.2° C. and an MFR of 2.97 g/10 min, while the soluble fraction at 0° C., where the dissolution of the olefin polymer was measured at various temperatures while continuously or gradually raising the temperature of the o-dichlorobenzene, was 26.1 wt % and the haze was 81.9%. The obtained propylene//ethylene/propylene block copolymer also contained 65.7 wt % of segment A (propylene homopolymer block component) and 34.3 wt % of segment B (propylene/ethylene copolymer block component). The ethylene unit content of segment B was 54.1 mol % and the MFR was 4.1 g/10 min. The polymerization activity of the catalyst was calculated to be 3500 g·polymer/g·Zr.

Example 8

Production of propylene//ethylene/propylene block copolymer

After nitrogen substitution of a stainless steel stirrer-equipped polymerization vessel with an interior volume of 1.5 L, 0.5 mmol of triethylaluminum (1 mol/L concentration n-hexane solution), 100 ml of hydrogen and 800 ml of liquefied propylene were loaded. After then raising the temperature of the polymerization vessel to 60° C., the preactivated catalyst obtained in Example 2 slurrified in 5 ml of n-hexane was injected into the polymerization vessel at 13.3 mg in terms of the supported catalyst prior to preactivation, together with 200 ml of liquefied propylene, and polymerization was initiated. After initiating polymerization, the temperature in the polymerization vessel was raised to and kept at 70° C., and the polymerization reaction was continued for one hour. After elapse of the polymerization time, the unreacted polymer was eliminated out of the system while lowering the temperature of the polymerization vessel to 25° C., and then a portion (30.7 g) of the reaction product was drawn out and used as a sample of the propylene polymer corresponding to segment A (propylene homopolymer block component).

Next, 0.5 mmol of triethylaluminum (1 mol/L concentration n-hexane solution) was added with the reaction product remaining in the polymerization vessel, the temperature in the polymerization vessel was raised to and kept at 50° C., an ethylene/propylene mixed gas (molar ratio: ethylene/propylene=50/50) was supplied to maintain an internal pressure of 1.0 MPa in the polymerization vessel, and gas-phase copolymerization of ethylene/propylene was continued for 290 minutes. After elapse of the polymerization time, supply of the ethylene/propylene mixed gas was interrupted, and the unreacted mixed gas was eliminated out of the system while lowering the temperature of the polymerization vessel to 25° C., to obtain 159.4 g of a particulate reaction product (propylene//ethylene/propylene block copolymer). The polymerization vessel was opened and observed after completion of the polymerization, but no lump polymer and no polymer adhesion on polymerization vessel wall was found.

The obtained propylene//ethylene/propylene block copolymer had an ethylene unit content of 5.2 mol %, a BD of 440 kg/m$^3$, an intrinsic viscosity ([η]w) of 1.46 dl/g, a Tm of 154.6° C. and an MFR of 4.96 g/10 min, while the soluble fraction at 0° C., where the dissolution of the olefin polymer was measured at various temperatures while continuously or gradually raising the temperature of the o-dichlorobenzene, was 10.2 wt % and the haze was 61.8%. The obtained propylene//ethylene/propylene block copolymer also contained 84.7 wt % of segment A (propylene homopolymer block component) and 15.3 wt % of segment B (ethylene/propylene copolymer block component). By calculation, the ethylene unit content of segment B was 30.9 mol % and the MFR was 115 g/10 min. The polymerization activity of the catalyst was calculated to be 2050 g·polymer/g·catalyst·hr in terms of one gram of the supported catalyst before preactivation.

Example 9

Propylene/ethylene copolymers were produced under the conditions for the propylene/ethylene copolymer of Example 4, but without addition of hydrogen, with a polymerization temperature of 60° C. and with ethylene fed into the reactor for an increase in pressure of 0.1, 0.3 and 0.4 MPa over the pressure before loading, and the relationship between the ethylene unit content and MFR of each of the obtained propylene/ethylene copolymers was examined. Table 1 shows the relationship between the ethylene unit content and the MFR of each propylene/ethylene copolymer, compared with the result for a propylene homopolymer obtained without introduction of ethylene. When a catalyst of the invention was used, the increase in MFR with introduction of ethylene was very slight, and therefore a propylene/ethylene copolymer with a low MFR was obtainable even with a high ethylene unit content. The superiority of the present invention will be even more apparent by comparison with the results for Comparative Example 3.

TABLE 1

Relationship between ethylene unit content and MFR

| Ethylene unit content (mol %) | MFR (g/10 min) |
| --- | --- |
| 0 | 0.18 |
| 1.9 | 0.25 |
| 5.6 | 0.49 |
| 7.2 | 0.36 |

Comparative Example 1

Synthesis of dimethylsilylenebis(2-methyl-4-phenyl-indenyl)zirconium dichloride racemate A dimethylsilylenebis(2-methyl-4-phenyl-indenyl) zirconium dichloride racemate was synthesized by the method described in Japanese Patent Kokai H6-100579.

Production of propylene homopolymer using dimethylsilylenebis(2-methyl-4-phenyl-indenyl)zirconium dichloride racemate as catalyst In an SUS autoclave there were loaded in order 1 L of toluene, a methylaluminoxane/toluene solution ("MMAO3A", product of Tosoh Akzo) (Al/Zr=10,000) and 3 ml (0.14×10$^{-6}$ mol) of a rac-dimethylsilylenebis(2-methyl-4-phenyl-indenyl)zirconium dichloride/toluene solution, and the mixture was heated to 30° C. Propylene was introduced under a pressure of 0.3 MPa for one hour of polymerization. After the polymerization, the polymer was filtered off and the catalyst component was decomposed with 1 liter of acidic methanol. This was followed by filtration, washing and drying in that order, to obtain 5.1 g of propylene homopolymer. The polymerization activity was 36 kg-polymer/mmol(Zr)·hr. Upon analysis of the obtained propylene homopolymer, the MFR was 0.004 g/10 min, the Mw/Mn ratio was 2.64 and the melting point was 157.0° C.

Comparative Example 2

Production of propylene homopolymer using dimethylsilylenebis(2-methyl-4-phenyl-indenyl)zirconium dichloride racemate as catalyst After adding a methylaluminoxane/toluene solution ("MMAO3A", product of Tosoh Akzo) to an SUS autoclave at 2.25×10$^{-3}$ moles in terms of Al, 1 L of liquefied propylene was added and the temperature was raised to 50° C. Separately, the dimethylsilylenebis(2-methyl-4-phenyl-indenyl) zirconium dichloride racemate synthesized in Example 1 (0.25×10$^{-6}$ mol) and a methylaluminoxane/toluene solution ("MMAO3A", product of Tosoh Akzo) (1.5×10$^{-3}$ moles in terms of Al) were reacted for 15 minutes, after which the reaction solution was injected into an autoclave to initiate polymerization reaction for propylene homopolymerization at 50° C. for 20 minutes. The polymerization reaction was suspended by addition of a small amount of methanol, and then the product was delimed with a strong alkali solution and dried to obtain 22.7 g of a propylene homopolymer. The polymerization activity was 272 kg-polymer/mmol(Zr)·hr. Upon analysis of the obtained propylene homopolymer, the melting point was 157.6° C.

Comparative Example 3

A preactivated supported metallocene catalyst was produced in the same manner as Example 2 except that a dimethylsilylenebis(2-methyl-4-phenyl-indenyl)zirconium dichloride racemate was used instead of the dimethylsilylenebis(2-(2-(5-methyl)-furyl)-4-phenylindenyl)zirconium dichloride racemate, a propylene/ethylene copolymer was produced in the same manner as Example 9 except that a preactivated supported metallocene catalyst produced using the dimethylsilylenebis(2-methyl-4-phenyl-indenyl)zirconium dichloride racemate obtained above was used instead of the preactivated supported metallocene catalyst used in Example 9, and the relationship between the ethylene unit content and the MFR of each of the propylene/ethylene copolymers was examined. Table 2 shows the relationship between the ethylene unit content and the MFR of each propylene/ethylene copolymer, compared with the result for a propylene homopolymer obtained without introduction of ethylene.

As clearly shown in Table 2, the MFR increased drastically with a higher ethylene unit content. That is, it was demonstrated that production of a low-MFR propylene/ethylene copolymer is extremely difficult when the ethylene unit content is high.

TABLE 2

Relationship between ethylene unit content and MFR

| Ethylene unit content (mol %) | MFR (g/10 min) |
|---|---|
| 0 | 0.05 |
| 1.9 | 1.8 |
| 5.4 | 7.2 |
| 6.6 | 8.7 |

Example 10

Synthesis of dimethylsilylenebis(2-(2-(5-methyl)-furyl)-4-(2-(5-methyl)-furyl)-indenyl)zirconium dichloride racemate (1) Synthesis of 2,7-dibromoindene Using a 200 ml Erlenmeyer flask, 7.00 g (35.89 millimoles) of 7-bromoindene produced by the method described in J. Org. Chem. 49, 4226–4237(1984) was dissolved in a mixed solvent of 1.42 g (79.00 millimoles) of distilled water and 70 ml of dimethyl sulfoxide. To this reaction solution there was added 7.67 g (43.07 millimoles) of N-bromosuccinimide while cooling on ice, and the mixture was then stirred for one hour at room temperature. After hydrolysis with distilled water while cooling on ice, extraction was performed several times with diethyl ether, and the extract was washed with saturated saline and then dried over anhydrous magnesium sulfate. After filtration of the magnesium sulfate, the solvent was distilled off under reduced pressure. The obtained product was transferred to a 200 ml Erlenmeyer flask and dissolved in 100 ml of toluene. To this solution there was added 0.68 g (3.59 millimoles) of p-toluenesulfonic acid hydrate, and the mixture was heated to reflux for 4 hours. After reflux, hydrolysis was performed with distilled water while cooling on ice, and extraction was performed several times with diethyl ether. The extract was washed once with a saturated sodium bicarbonate aqueous solution, washed once with saturated saline, and then dried over anhydrous magnesium sulfate. After drying, the magnesium sulfate was filtered off, the solvent was distilled off under reduced pressure, and purification was performed with a silica gel column to obtain 6.6 g of 2,7-dibromoindene as white crystals (67% yield).

(2) Synthesis of 2,7-bis(2-(5-methyl)-furyl)-indene

In a 500 ml three-necked flask there were loaded 8.84 g (107.67 millimoles) of 2-methylfuran and 100 ml of tetrahydrofuran under a nitrogen stream. To this solution there was added dropwise 40.5 ml (107.67 millimoles) of an n-butyl-lithium/hexane solution (2.66 N) at –78° C., and the mixture was stirred at room temperature for 2 hours. After then adding dropwise to the reaction solution 14.7 g (107.67 millimoles) of zinc chloride ($ZnCl_2$) dissolved in 150 ml of tetrahydrofuran at –78° C., the mixture was further stirred at room temperature overnight. To this solution there was added dropwise 6.50 g (23.72 millimoles) of 2,7-dibromoindene dissolved in 70 ml of tetrahydrofuran at –78° C., and then 2.74 g (2.37 millimoles) of tetrakis(triphenylphosphine) palladium (0) dissolved in 50 ml of tetrahydrofuran was added dropwise and the mixture was heated to reflux at 50° C. for 12 hours. After reflux, hydrolysis was performed with a saturated aqueous solution of ammonium chloride, distilled water was added, extraction was performed several times with diethyl ether, and then the extract was washed once with saturated saline and dried over anhydrous magnesium sulfate. After drying, the magnesium sulfate was filtered off, the solvent was distilled off under reduced pressure, and purification was performed with a silica gel column to obtain 6.32 g of 2,7-bis(2-(5-methyl)-furyl)-indene as an orange solid (96% yield).

(3) Synthesis of dimethylbis[2,4-bis(2-(5-methyl)-furyl)-indenyl]silane

Using a 300 ml three-necked flask as the reactor, under a nitrogen stream, 6.2 g (22.44 millimoles) of 2,7-bis (2-(5-methyl)-furyl)-indene and 219 mg (2.24 millimoles) of copper (I) cyanide (CUCN) were dissolved in 80 ml of tetrahydrofuran. To this solution there was added dropwise 8.44 ml (22.44 millimoles) of an n-butyllithium/hexane solution (2.66 N) at –40° C., and the mixture was stirred at –40° C. for 2 hours. After then adding dropwise to the reaction solution 1.45 g (11.22 millimole) of dimethyldichlorosilane dissolved in 20 ml of tetrahydrofuran at –40° C., the mixture was further stirred at room temperature overnight. Celite was then used for filtration to remove the copper catalyst, and after hydrolysis with a saturated aqueous solution of ammonium chloride, distilled water was added, extraction was performed several times with diethyl ether, and then the extract was washed once with saturated saline and dried over anhydrous magnesium sulfate. After drying, the magnesium sulfate was filtered off, the solvent was distilled off under reduced pressure, and purification was performed with a silica gel column to obtain 3.59 g of a mixture of the meso form and racemic form of dimethylbis [2,4-bis(2-(5-methyl)-furyl)-indenyl]silane (meso:racemic=50:50) as a brown oil (53% yield).

(4) Synthesis of dimethylsilylenebis(2-(2-(5-methyl)-furyl)-4 -(2-(5-methyl)-furyl)-indenyl)zirconium dichloride racemate Using a 100 ml flask as the reactor, under a nitrogen stream, 3.55 g (5.83 millimoles) of dimethylbis[2,4-bis(2-(5-methyl)-furyl)-indenyl]silane was dissolved in 40 ml of diethyl ether. To this solution there was added dropwise 4.4 ml (11.66 millimoles) of an n-butyllithium/hexane solution (2.66 N) at −78° C., and the mixture was stirred at a room temperature overnight. The diethyl ether solvent was distilled off under reduced pressure and the residue was dissolved in 40 ml of toluene. The reaction solution was solidified with liquefied nitrogen, and then a solution of 1.36 g (5.83 millimoles) of zirconium tetrachloride in 30 ml of toluene was added dropwise and the mixture was stirred at room temperature overnight. After stirring, the mixture was centrifuged to remove the lithium salt, and the solvent was distilled off under reduced pressure. As a result of $^1$H-NMR measurement of the product, the meso:racemic mixture ratio was found to be meso:racemic=0:100. The product was extracted with hexane, the remaining brown powder was further extracted with diethyl ether and recrystallization from the reaction solution yielded 830 mg of dimethylsilylenebis(2-(2-(5-methyl)-furyl)-4-(2-(5-methyl)-furyl)-indenyl)zirconium dichloride racemate as a reddish brown powder (18% yield). The results of $^1$H-NMR identification of the dimethylsilylenebis(2-(2-(5-methyl)-furyl)-4-(2-(5-methyl)-furyl)-indenyl)zirconium dichloride racemate were as follows.

<Identification by $^1$ H-NMR(CDCl$_3$)>

δ 1.10 (s, 6 H), δ 2.34 (s, 6 H), δ 2.42 (s, 6 H), δ 6.04 (dd, 2 H), δ 6.07 (dd, 2 H), δ 6.29 (d, 2 H), δ 6.70 (d, 2 H), δ 6.77 (dd, 2 H), δ 7.29 (s, 2 H), δ 7.61 (d, 2H)

Production of propylene homopolymer using dimethylsilylenebis(2-(2-(5-methyl)-furyl)-4-(2-(5-methyl) -furyl)-indenyl)zirconium dichloride racemate as catalyst component In an SUS autoclave there were loaded in order 1 L of toluene, a methylaluminoxane/toluene solution ("MMAO3A", product of Tosoh Akzo) (Al/Zr=10,000) and 3 ml (2.03×10$^{-6}$ mol) of a rac-dimethylsilylenebis(2-(2-(5-methyl)-furyl) -4-(2-(5-methyl)-furyl)-indenyl)zirconium dichloride/toluene solution, and the mixture was heated to 30° C. Propylene was introduced under a pressure of 0.3 MPa for one hour of polymerization. After the polymerization, the polymer was filtered off and the catalyst component was decomposed with 1 liter of hydrochloric acidic methanol. This was followed by filtration, washing and drying in that order, to obtain 16.6 g of propylene homopolymer. The polymerization activity was 8.2 kg-polymer/mmol(Zr)·hr. Upon analysis of the obtained propylene homopolymer, the MFR was 2.0 g/10 min, the Mw was 2.61×10$^?$ g/mol, the Mw/Mn ratio was 2.07, the melting point was 147.8° C., the isotactic pentad factor (I$_5$) was 0.934, the proportion of the number of moles of the propylene unit derived from 2,1-insertion reaction of the propylene monomer with respect to the total number of moles of the propylene unit of the propylene homopolymer was 0.74 mol %, and the proportion of the number of moles of the propylene unit derived from 1,3-insertion reaction of the propylene monomer with respect to the total number of moles of the propylene unit of the propylene homopolymer was 0.11 mol %.

Example 11

Synthesis of dimethylsilylenebis(2-(2-(5-methyl)-furyl)-4-isopropyl-indenyl)zirconium dichloride racemate (1) Synthesis of 7-isopropylindene Using a 300 ml three-necked flask as the reactor, under a nitrogen stream, 1.36 g (2.57 millimoles) of [1,2-bis(diphenylphosphino)ethane]dichloronickel(II) was dissolved in 20 ml of tetrahydrofuran. To this suspension there was added a solution of 10 g (51.30 millimoles) of 7-bromoindene in 100 ml of tetrahydrofuran, prepared based on the method described in J. Org. Chem. 49, 4226–4237(1984). After dropwise addition of 51 ml (102.60 millimoles) of isopropylmagnesium bromide (2N) to the mixed solution while cooling on ice, the mixture was heated to reflux for 20 hours. After reflux, hydrolysis was performed with a saturated aqueous solution of ammonium chloride, distilled water was added, extraction was performed several times with diethyl ether, and then the extract was washed once with saturated saline and dried over anhydrous magnesium sulfate. After drying, the magnesium sulfate was filtered off and the solvent was purified with a silica gel column to obtain 7.14 g of 7-isopropylindene as a yellow oil (88% yield).

(2) Synthesis of 7-isopropyl-2-bromo-indene

Using a 200 ml Erlenmeyer flask as the reactor, 7.00 g (44.20 millimoles) of 7-isopropylindene was dissolved in a mixed solvent of 0.91 g (106.08 millimoles) of distilled water and 60 ml of dimethyl sulfoxide. To this reaction solution there was added 9.44 g (53.03 millimoles) of N-bromosuccinimide while cooling on ice, and the mixture was then stirred for one hour at room temperature. After hydrolysis with distilled water while cooling on ice, extraction was performed several times with diethyl ether, and the extract was washed with saturated saline and then dried over anhydrous magnesium sulfate. After filtration of the magnesium sulfate, the solvent was distilled off under reduced pressure. The obtained product was transferred to a 200 ml Erlenmeyer flask and dissolved in 70 ml of toluene. To this solution there was added 0.84 g (4.42 millimoles) of p-toluenesulfonic acid hydrate, and the mixture was heated to reflux for 4 hours. After reflux, hydrolysis was performed with distilled water while cooling on ice, and extraction was performed several times with diethyl ether. The extract was washed once with a saturated sodium bicarbonate aqueous solution, washed once with saturated saline, and then dried over anhydrous magnesium sulfate. After drying, the magnesium sulfate was filtered off, the solvent was distilled off under reduced pressure, and purification was performed with a silica gel column to obtain 10.2 g of 7-isopropyl-2-bromo-indene as a reddish brown oil (97% yield).

(3) Synthesis of 2-(2-(5-methyl)-furyl)-7-isopropyl-indene

Using a 500 ml three-necked flask as the reactor, 6.92 g (84.34 millimoles) of 2-methylfuran was dissolved in 80 ml of tetrahydrofuran under a nitrogen stream. To this solution there was added dropwise 31.7 ml (84.34 millimoles) of an n-butyllithium/hexane solution (2.66 N) at −78° C., and the mixture was stirred at room temperature for 2 hours. After then adding dropwise to the reaction solution 11.5 g (84.34 millimoles) of zinc chloride (ZnCl$_2$) dissolved in 120 ml of tetrahydrofuran at −78° C., the mixture was further stirred at room temperature overnight. To this solution there was added dropwise 10.0 g (42.17 millimoles) of 7-isopropyl-2-bromo-indene dissolved in 100 ml of tetrahydrofuran at −78° C., and then 2.43 g (0.21 millimole) of tetrakis(triphenylphosphine) palladium (0) dissolved in 30 ml of tetrahydrofuran was added dropwise and the mixture was heated to reflux at 50° C. for 12 hours. After reflux, hydrolysis was performed with a saturated aqueous solution of ammonium chloride, distilled water was added, extraction was performed several times with diethyl ether, and then the extract was washed once with saturated saline and dried over anhydrous magnesium sulfate. After drying, the magnesium sulfate was filtered off, the solvent was distilled off under reduced pressure, and purification was performed with a silica gel column to obtain 7.80 g of 2-(2-(5-methyl)-furyl)-7-isopropyl-indene as a brown oil (83% yield).

(4) Synthesis of dimethylbis[2-(2-(5-methyl)-furyl)-4-isopropylindenyl]silane

Using a 300 ml three-necked flask as the reactor, under a nitrogen stream, 8.00 g (33.57 millimoles) of 2-(2-(5-methyl)-furyl)-7-isopropyl-indene and 301 mg (3.36 millimoles) of copper (I) cyanide (CuCN) were dissolved in 80 ml of tetrahydrofuran. To this solution there was added dropwise 12.62 ml (33.57 millimoles) of an n- butyllithium/hexane solution (2.66 N) at −40° C., and the mixture was stirred at −40° C. for 2 hours. After then adding dropwise to the reaction solution 2.17 g (16.79 millimoles) of dimethyldichlorosilane dissolved in 20 ml of tetrahydrofuran at −40° C., the mixture was further stirred at room temperature overnight. After stirring, Celite was used for filtration to remove the copper catalyst, and after hydrolysis with a saturated aqueous solution of ammonium chloride, distilled water was added, extraction was performed several times with diethyl ether, and then the extract was washed once with saturated saline and dried over anhydrous magnesium sulfate. After drying, the magnesium sulfate was filtered off, the solvent was distilled off under reduced pressure, and purification was performed with a silica gel column to obtain 5.6 g of a mixture of the meso form and racemic form of dimethylbis[2-(2-(5-methyl)-furyl)-4-isopropylindenyl]silane (meso:racemic=50:50) as a brown oil (63% yield).

(5) Synthesis of dimethylsilylenebis(2-(2-(5-methyl)-furyl) -4-isopropyl-indenyl)zirconium dichloride racemate Using a 100 ml flask as the reactor, under a nitrogen stream, 4.0 g (7.51 millimoles) of dimethylbis[2-(2-(5-methyl)-furyl)-4-isopropylindenyl]silane was dissolved in 40 ml of diethyl ether. To this solution there was added dropwise 5.7 ml (15.02 millimoles) of an n-butyllithium/hexane solution (2.66 N) at −78° C., and the mixture was stirred at a room temperature overnight. The diethyl ether solvent was distilled off under reduced pressure and the residue was dissolved in 40 ml of toluene. The reaction solution was solidified with liquefied nitrogen, and then a solution of 1.75 g (7.51 millimoles) of zirconium tetrachloride in 40 ml of toluene was added dropwise and the mixture was stirred at room temperature overnight. After stirring, the mixture was centrifuged to remove the lithium salt, and the solvent was distilled off under reduced pressure. The residue was a mixture of the meso form and racemic form (meso:racemic=30:70). The residue was extracted with hexane, and recrystallization of the hexane solution from the mother liquor yielded 1.40 g of dimethylsilylenebis(2-(2-(5-methyl)-furyl)-4-isopropyl-indenyl) zirconium dichloride racemate as a yellow powder (27% yield). The results of $^1$H-NMR identification of the dimethylsilylenebis(2-(2-(5-methyl)-furyl)-4-isopropyl-indenyl) zirconium dichloride racemate were as follows.

<Identification by $^1$ H-NMR(CDCl$_3$)>δ=1.11 (s, 6 H), δ 1.24 (d, 6 H), δ 1.37 (d, 6 H), δ 2.43 (s, 6 H) δ 3.11 (sp, 2 H), δ 6.07 (d, 2 H), δ 6.28 (d, 2 H), δ 6.70 (dd, 2 H), δ 6.77 (d, 2 H), δ 6.97 (s, 2 H), δ 7.14(d, 2 H).

Production of propylene homopolymer using dimethylsilylenebis(2-(2-(5-methyl)-furyl)-4-isopropyl-indenyl)zirconium dichloride racemate as catalyst component In an SUS autoclave there were loaded in order 1 L of toluene, a methylaluminoxane/toluene solution ("MMAO3A", product of Tosoh Akzo) (Al/Zr=10,000) and 3 ml (0.30×10$^{-6}$ mol) of a dimethylsilylenebis(2-(2-(5-methyl)-furyl))-4-(2-(5-methyl)-furyl)-indenyl)zirconium dichloride racemate/toluene solution, and the mixture was heated to 30° C. Propylene was introduced under a pressure of 0.3 MPa for one hour of polymerization. After the polymerization, the polymer was filtered off and the catalyst component was decomposed with 1 liter of hydrochloric acidic methanol. This was followed by filtration, washing and drying in that order, to obtain 15.7 g of propylene homopolymer. The polymerization activity was 53 kg-polymer/mmol(Zr)·hr. Upon analysis of the obtained propylene homopolymer, the MFR was 0.23 g/10 min, the Mw/Mn ratio was 2.40 and the melting point was 157.1° C.

Example 12

Synthesis of dimethylsilylenebis(2-methyl-4-(2-(5-methyl)-thienyl)-4-hydroazulenyl)zirconium dichloride (1) Synthesis of 2-methyl-4-(2-(5-methyl)-thienyl)-dihydroazulene After adding 13.8 g (0.14 mol) of 2-methylthiophene and 100 ml of diethyl ether into a 500 ml glass reactor, the mixture was cooled to −70° C. in a dry ice/methanol bath. Next, 90 ml (0.14 mol) of a 1.57 mol/l n-butyllithium-hexane solution was added dropwise thereto. After the dropwise addition, the mixture was stirred for 16 hours while gradually returning it to room temperature. It was again cooled to −40° C. in a dry ice/methanol bath, and 100 ml of a hexane solution containing 10 g (70 millimoles) of 2-methylazulene was added dropwise. After the dropwise addition, the mixture was returned to room temperature, stirred for 3 hours and heated to reflux for 6 hours. The reaction solution was cooled to −20° C. in a dry ice/methanol bath, and 50 ml of dilute hydrochloric acid was added dropwise. The reaction solution was then transferred to a separatory funnel and washed with saline solution to neutrality, after which anhydrous sodium sulfate was added thereto and the mixture was allowed to stand overnight to dryness. The anhydrous sodium sulfate was filtered out, the solvent was distilled off under reduced pressure, and purification was performed with a silica gel column to obtain 6.7 g of 2-methyl-4-(2-(5-methyl)-thienyl) -dihydroazulene as a dark green liquid (40% yield). The structure was confirmed by NMR.

(2) Synthesis of dimethylbis(2-methyl-4-(2-(5-methyl)-thienyl)-1,4-dihydroazulenyl)silane After adding 6.0 g (25 millimoles) of 2-methyl-4-(2-(5-methyl)-thienyl)-dihydroazulene, 150 ml of hexane and 30 ml of diethyl ether to a 500 ml glass reactor, the mixture was cooled to −70° C. in a dry ice/methanol bath. Next, 24 ml (25 millimoles) of a 1.04 mol/l methyllithium/diethyl ether solution was added dropwise thereto. After the dropwise addition, the mixture was returned to room temperature, stirred for one hour and then heated at 50° C. for one hour. After cooling to room temperature, 100 ml of tetrahydrofuran and 0.1 ml (1.3 millimoles) of 1-methylimidazole were added, the mixture was cooled to −70° C. in a dry ice/methanol bath, and 40 ml of a tetrahydrofuran solution containing 1.5 ml (12 millimoles) of dimethyldichlorosilane was added dropwise. After the dropwise addition, the mixture was stirred for 16 hours while gradually returning it to room temperature.

Distilled water was added to the reaction solution which was then transferred to a separatory funnel and washed with saline solution to neutrality. Anhydrous sodium sulfate was added thereto, and the mixture was allowed to stand overnight to dry the reaction solution. The anhydrous sodium sulfate was filtered out, the solvent was distilled off under reduced pressure, and purification was performed with a silica gel column to obtain 5.2 g of dimethylbis(2-methyl-4-(2-(5-methyl)-thienyl)-1,4-dihydroazulenyl)silane as a yellow-green solid (78% yield).

(3) Synthesis of dimethylsilylenebis(2-methyl-4-(2-(5-methyl)-thienyl)-4-hydroazulenyl)zirconium dichloride After adding 6.2 g (12 millimoles) of dimethylbis(2-methyl-4-(2-(5-methyl)-thienyl)-1,4-dihydroazulenyl)silane and 200 ml of diethyl ether to a 500 ml glass reactor, the mixture was cooled to −70° C. in a dry ice/methanol bath. Next, 15 ml (24 millimoles) of a 1.57 mol/l n-butyllithium-hexane solution was added dropwise thereto. After the dropwise addition, the mixture was returned to room temperature and stirred for one hour stirred for 16 hours. The solvent of the reaction solution was distilled off under reduced pressure, after which 300 ml of toluene and 15 ml of diethyl ether were added and the mixture was cooled to −70° C. in a dry ice/methanol bath. To this there was added 2.7 g (12 millimoles) of zirconium tetrachloride. The mixture was then stirred for 16 hours while gradually returning it to room temperature. Analysis by $^1$H-NMR at this stage indicated that a mixture of the racemic form and the meso form (racemic:meso=60:40) had been obtained.

The solvent was distilled off under reduced pressure, and recrystallization was performed with dichloromethane/hexane to obtain 0.7 g of dimethylsilylenebis(2-methyl-4-(2-(5-methyl)-thienyl)-4-hydroazulenyl)zirconium dichloride racemate (7% yield) with a purity of $\geqq$99%. The $^1$H-NMR data for the obtained racemic form and meso form are as follows.

<Identification by $^1$ H-NMR(CDCl$_3$)>

Racemic: δ 1.00 (s, 6H), δ 2.21 (s, 6H), δ 2.48 (s, 6H) δ 5.10 (d, 2H), δ 5.88–5.95 (m, 4H), δ 6.15 (dd, 2H), δ 6.20 (s, 2H), δ 6.65 (dd, 2H), δ 6.80 (d, 2H), δ 6.91 (d, 2H).

Meso: δ 0.98 (s, 3H), δ 1.01 (s, 3H), δ 2.23 (s, 6H), δ 2.46 (s, 6H), δ 5.14 (d, 2H), δ 5.88–5.95 (m, 4H), δ 6.15 (dd, 2H), δ 6.11 (s, 2H), δ 6.62 (dd, 2H), δ 6.78 (d, 2H), δ 6.89 (d, 2H).

Production of propylene homopolymer using dimethylsilylenebis(2-methyl-4-(2-(5-methyl)-thienyl)-4-hydroazulenyl)zirconium dichloride racemate as catalyst component In an SUS autoclave there were loaded in order 1 L of toluene, a methylaluminoxane/toluene solution ("MMAO3A", product of Tosoh Akzo) (Al/Zr=10,000) and 3 ml (0.30×10$^{-6}$ mol) of dimethylsilylenebis(2-methyl-4-(2-(5-methyl)-thienyl) -4-hydroazulenyl)zirconium dichloride racemate/toluene solution, and the mixture was heated to 30° C. Propylene was introduced under a pressure of 0.3 MPa for one hour of polymerization. After the polymerization, the polymer was filtered off and the catalyst component was decomposed with 1 liter of acidic methanol. This was followed by filtration, washing and drying in that order, to obtain 4.2 g of propylene homopolymer. The polymerization activity was 14 kg-polymer/mmol(Zr)·hr. Upon analysis of the obtained propylene homopolymer, the MFR was 0.05 g/10 min, the Mw was 9.74×10$^5$ g/mol, and the melting point was 157.8° C.

Comparative Example 4

Production of propylene homopolymer using dimethylsilylenebis(2-methyl-4-phenyl-4-hydroazulenyl) zirconium dichloride racemate as catalyst component In an SUS autoclave there were loaded in order 1 L of toluene, a methylaluminoxane/toluene solution ("MMAO3A", product of Tosoh Akzo) (Al/Zr=10,000) and 3 ml (0.30×10$^{-6}$ mol) of dimethylsilylenebis(2-methyl-4-phenyl-4-hydroazulenyl) zirconium dichloride racemate/toluene solution synthesized based on the method described in Example 1 of Japanese Patent Kokai H10-226712, and the mixture was heated to 30° C. Propylene was introduced under a pressure of 0.3 MPa for one hour of polymerization. After the polymerization, the polymer was filtered off and the catalyst component was decomposed with 1 liter of acidic methanol. This was followed by filtration, washing and drying in that order, to obtain 5.42 g of propylene homopolymer. The polymerization activity was 19 kg-polymer/ mmol(Zr)·hr. Upon analysis of the obtained propylene homopolymer, the MFR was 0.04 g/10 min, the Mw was 1.24×10$^6$ g/mol, and the melting point was 154.0° C.

By comparison with Example 12 and Comparative Example 4, it is obvious that it is possible to produce higher stereoregular propylene homopolymers, that is, propylene homopolymers with higher melting point by metallocene catalyst system having as substituents a methyl-thienyl group than by metallocene catalyst system having a phenyl group instead of the methyl-thienyl group.

According to the present invention it is possible to produce highly stereoregular olefin polymers at a high degree of polymerization activity.

Moreover, the invention gives propylene/ethylene copolymers of sufficiently high molecular weight even with high ethylene contents.

The olefin polymers obtained by the invention have few o-dichlorobenzene soluble components, so that molded articles obtained from them exhibit low tackiness and excellent transparency.

What is claimed is:

1. A metallocene compound represented by the following general formula (2):

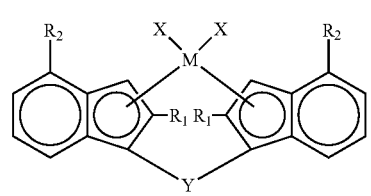

wherein
M represents a titanium atom, a zirconium atom or a hafnium atom;
Y is a bridge group representing methylene, ethylene, tetraalkylethylene with $C_1$–$C_6$ alkyl groups, dialkylmethylene with $C_1$–$C_6$ alkyl groups, or a divalent bridge group containing a silicon atom, a germanium atom, an oxygen atom, a nitrogen atom, a phosphorus atom or a boron atom;
X represents a halogen atom, $C_1$–$C_6$ alkyl, $C_6$–$C_{16}$ aryl, alkylaryl having a $C_1$–$C_6$ alkyl group and a $C_6$–$C_{16}$ aryl group, or arylalkyl having a $C_6$–$C_{16}$ aryl group and a $C_1$–$C_6$ alkyl group;
each $R_1$ independently represents $C_1$–$C_6$ alkyl, a $C_1$–$C_6$ halogen-containing alkyl group, a $C_1$–$C_6$ silicon-containing alkyl group, $C_6$–$C_6$ aryl, a $C_6$–$C_{16}$ halogen-containing aryl group, a 2-furyl group, a substituted 2-furyl group, a 2-thienyl group, a substituted 2-thienyl group, a 2-furfuryl group or a substituted 2-furfuryl group; and
each $R_2$ independently represents $C_1$–$C_6$ alkyl, a $C_1$–$C_6$ halogen-containing alkyl group, a $C_1$–$C_6$ silicon-containing alkyl group, $C_6$–$C_{16}$ aryl substituted with one or more $C_1$–$C_6$ hydrocarbon groups, a $C_6$–$C_{16}$ halogen-containing aryl group, a 2-furyl group, a substituted 2-furyl group, a 2-thienyl group, a substituted 2-thienyl group, a 2-furfuryl group or a substituted 2-furfuryl group, with the proviso that at least one of the two $R_1$'s is a substituted 2-furyl group or a substituted 2-thienyl group.

2. A metallocene compound according to claim 1, wherein in general formula (2), Y is methylene, ethylene or dialkylsilylene with $C_1$–$C_6$ alkyl groups; each $R_1$ is independently a substituted 2-furyl group or a substituted 2-thienyl group; and each $R_2$ is independently $C_1$–$C_6$ alkyl, $C_6$–$C_{16}$ aryl substituted with one or more $G_1$–$C_6$ hydrocarbon groups, a $C_6$–$C_{16}$ halogen-containing aryl group, a 2-furyl group, a substituted 2-furyl group, a 2-thienyl group, a substituted 2-thienyl group, a 2-furfuryl group or a substituted 2-furfuryl group.

3. A metallocene compound according to claim 1, wherein in general formula (2), each $R_1$ and each $R_2$ is independently a substituted 2-furyl group or a substituted 2-thienyl group.

* * * * *